United States Patent [19]

Egawa et al.

[11] Patent Number: 5,616,812
[45] Date of Patent: Apr. 1, 1997

[54] METHOD OF PRODUCING A POLYVINYL ETHER COMPOUND

[75] Inventors: Tatsuya Egawa; Yasuhiro Kawaguchi; Kenji Mogami; Nobuaki Shimizu, all of Sodegaura, Japan

[73] Assignee: Idemitsu Kosan Co., Ltd., Tokyo, Japan

[21] Appl. No.: 305,797

[22] Filed: Sep. 13, 1994

Related U.S. Application Data

[62] Division of Ser. No. 66,229, May 25, 1993, abandoned.

[30]    Foreign Application Priority Data

Jun. 4, 1992  [JP]  Japan ..................... 4-143922
Sep. 7, 1992  [JP]  Japan ..................... 4-237842

[51] Int. Cl.$^6$ ..................... C07C 43/30; C07C 43/32
[52] U.S. Cl. ..................... 568/598; 568/673
[58] Field of Search ..................... 568/598, 673

[56]    References Cited

U.S. PATENT DOCUMENTS

| | | | |
|---|---|---|---|
| 2,165,962 | 7/1939 | Mueller-Cundradi et al. | 260/615 |
| 2,487,525 | 11/1949 | Copenhaver | 260/615 |
| 2,502,433 | 4/1950 | Copenhaver | 568/601 |
| 2,590,598 | 3/1952 | Copenhaver | 260/615 |
| 3,121,120 | 2/1964 | Montagna et al. | |
| 3,541,015 | 11/1970 | Schultz et al. | |
| 4,161,405 | 7/1979 | Crivello | 568/673 |
| 4,837,271 | 6/1989 | Brindopke | 525/330.3 |

*Primary Examiner*—Porfirio Nazario-Gonzalez
*Assistant Examiner*—Rosalynd A. Williams
*Attorney, Agent, or Firm*—Antonelli, Terry, Stout & Kraus, LLP

[57]    ABSTRACT

A method of production of polyvinyl ether compound by which the polyvinyl ether compound having a desired degree of polymerization is produced reliably, safely and efficiently and a novel polyvinyl ether compound useful as lubricating oil for compression-type refrigerators, electric insulation oil and the like are disclosed. The method of production of the present invention is a method of producing a polyvinyl ether compound which comprises polymerizing a vinyl ether compound in the presence of a Lewis acid catalyst and a specific acetal or a method of producing a polyvinyl ether compound which comprises forming an acetal by reaction of a vinyl ether compound with a specific alcohol in the presence of a Lewis acid catalyst, then adding the vinyl ether compound to the acetal and polymerizing the vinyl ether compound. The polyvinyl ether compound of the present invention is homopolymer or a copolymer of an alkyl vinyl ether comprising the constituting unit expressed by the general formula:

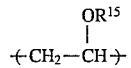

($R^{15}$: an alkyl group of $C_1$~$C_3$) and having weight average molecular weight of 300 to 1200 and one end having a specific structure.

1 Claim, 23 Drawing Sheets

METHOD OF PRODUCING A POLYVINYL ETHER COMPOUND

This application is a Divisional application of application Ser. No. 066,229, filed May 25, 1993, now abandoned.

BACKGROUND OF THE INVENTION

1. Field of the Invention

The present invention is related to a novel method of production of polyvinyl ether compounds and a novel polyvinyl ether compound. More particularly, the present invention is related to a method of producing a polyvinyl ether compound having a desired degree of polymerization reliably, safely, efficiently and industrially advantageously in the production of the polyvinyl ether compound having a wide range of applications as solvent, lubricating oil, adhesive material, resin and the like and a novel polyvinyl ether compound useful as lubricating oil for compression-type refrigerators, electric insulation oil, organic solvent, surface active agent and the like.

2. Description of the Related Arts

According to "Gosei Kobunshi III" (edited by Shunsuke Murahashi, Minoru Imoto and Hisashi Tani, published by Asakura Shoten), vinyl ether compounds are shown to be polymerized by a radical, a cation and irradiation. When a vinyl ether polymer having a desired degree of polymerization is produced by these methods, control of the degree of polymerization is generally made by adjusting amount of a radical initiator relative to the amount of the monomer in the case of the radical polymerization and by adjusting amount of an acid catalyst relative to the amount of the monomer in the case of the cationic polymerization. A polymer having a lower degree of polymerization can be produced by using a larger amount of the radical initiator or the acid catalyst relative to the amount of the monomer. However, when a polymer having a relatively low degree of polymerization is produced by these methods, a large amount of the radical initiator is required in the case of the radical polymerization and the method is economically unfavorable. Furthermore, a large amount of the radical initiator is contained at the initiated end of the formed polymer and there is the possibility that the proper physical properties of the vinyl ether polymer are adversely effected to a large extent. A large amount of the acid catalyst is required also in the case of the cationic polymerization and the method is economically unfavorable. Furthermore, problems such as side reactions, coloring and the like caused by the large amount of the acid catalyst arise.

On the other hand, as a method of producing a polymer having a relatively low degree of polymerization by using a small amount of catalyst, it was shown in Trans. Faraday Soc., Volume 43, Page 112 (1947) and in Trans. Faraday Soc., Volume 45, Pages 425 and 436 (1949) that, when reaction is conducted by adding n-butyl alcohol to the polymerization system consisting of n-butyl vinyl ether, tin tetrachloride and petroleum ether, viscosity of the polymer obtained is varied to a great extent. However, according to the technology disclosed in these references, the reaction used a large amount of petroleum ether as the solvent for n-butyl vinyl ether and the method is not desirable as an industrial process. Moreover, the reduced viscosity ($\eta_{sp/c}$) is as large as 1.7 dl/g and it is not clear whether a polymer of lower molecular weight can be produced.

It is also shown in Zhur. Priklad. Khim., Volume 25, Page 102 (1952), Chemical Abstracts, Volume 46, Page 11097 (1952), Otdel. Nauk, 1953, Page 1056, and Chemical Abstracts, Volume 49, Page 2299 (1955) that a polymer having the molecular weight of 1,545 to 5,488 could be obtained by slowly dropping a catalyst of 5% $FeCl_3 \cdot 6H_2O$-butanol solution into various kinds of vinyl ethers. Also, it was reported that, by polymerizing n-butyl vinyl ether in a system of 20% $FeCl_3 \cdot 6H_2O$, butanol solution catalyst and n-butyl ether solvent, polymers having molecular weight of 976 and 3,525 were obtained because of the difference of the butanol concentration [Zhur. Obshchei Khim., Volume 18, Page 1452 (1948) and Chemical Abstracts, Volume 43, Page 995 (1949)]. Similarly, it was reported that a mixture of polymers having molecular weights of 682 and 2,112 was obtained by the reaction of a mixture of butyl vinyl ether, 5% $FeCl_3$-butanol solution catalyst and butanol at 100° C. for 2 hours [Otdel. Khim. Nauk, 1954, Pages 362 to 369, and Chemical Abstracts, Volume 49, Page 4508 (1955)].

However, in the examples of reactions described above, the reaction was conducted by dropping a catalyst into butyl vinyl ether or by heating a mixture of butyl vinyl ether, butanol and a catalyst. When scale of the reaction system is increased, removal of the heat becomes a problem and control of the reaction temperature is difficult, the reaction becoming even dangerous because of uncontrollable reaction. It is known that vinyl ether compounds react very easily, sometimes explosively, by the cationic polymerization and the heat of the reaction generated is very large. For example, the heat of reaction of n-butyl vinyl ether is 60 KJ/mol [J. Brndrup; E. H. Immergut, "Polymer Handbook", Third Edition II/299 (WILEY, INTERSCIENCE)]. Therefore, for producing a considerable amount of polymer by these methods, a method in which the vinyl ether compound is diluted with a large amount of solvent or a method in which the reaction is conducted in a very small scale and number of batch of the reaction is increased must be adopted. These methods are not economical as industrial processes and are not preferable.

It was reported that the dimer (VII), the trimer (VIII) and the tetramer (IX) (each having an acetal end structure) can be synthesized by the following method: 5% $FeCl_3$-butanol solution catalyst is added to acetaldehyde dibutyl acetal; butyl vinyl ether is dropped to the mixture while the mixture is kept at 50° C. to synthesize the compounds (VII) and (VIII):

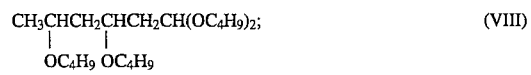

and then the compound (VII) is treated with butyl vinyl ether by the same method to obtain the compound (VIII) and a small amount of the compound (IX):

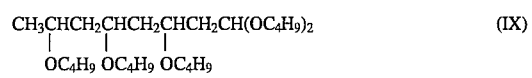

(Otdel. Khim. Nauk, 1955, Pages 140 to 145). However, it is not clear whether polybutyl vinyl ether compounds having larger molecular weight can be synthesized by the above technology. Moreover, for synthesizing the compound (IX), it is necessary that a mixture of the compounds (VII) and (VIII) is synthesized from acetaldehyde dibutyl acetal and the compound (VII) is separated by distillation or the like method and used as the material for the reaction with butyl vinyl ether. This means that acetaldehyde dibutyl acetal is used as the material for synthesis of the mixture of the compounds (VII) and (VIII) and two steps of the reaction and one operation of separation are required. Thus, for industrially synthesizing polybutyl vinyl ether compounds having larger degree of polymerization, the operation is too much complicated and not realistic.

It was also reported that, in the polymerization of methyl vinyl ether in toluene solvent by using boron trifluoride diethyl etherate as the catalyst at −78° C., intrinsic viscosity [η] of the formed polymer is decreased to a great degree by addition of methanol [Kobunshi Kagaku, Volume 18, No. 192, Page 267 (1961)]. However, the reaction is conducted at −78° C. according to the technology disclosed in this reference. A cooling facility of a large scale is required for industrial application of this process and the process is not preferable. Furthermore, the intrinsic viscosity [η] shown in the reference is as large as 0.3 and it is not clear whether polymer having lower molecular weight can be produced.

Thus, it is the real situation that a method of polymerizing a vinyl ether compound which can be applied widely in the range from a low degree of polymerization to a high degree of polymerization and is furthermore applied safely and reliably has not been discovered yet. Development of such a method is strongly desired.

Compression-type refrigerators are generally constituted with a compressor, a condenser, an expansion valve and an evaporator and has a structure that mixed fluid of refrigerant and lubricating oil is circulated in this closed system. In the compression-type refrigerator generally temperature is 50° C. or more in the compressor and about −40° C. in the refrigerating chamber although the temperature is varied depending on the kind of apparatus. Therefore, it is generally required that the refrigerant and the lubricating oil are circulated in the system without causing phase separation in the range of temperature of −40° C. to +50° C. When the phase separation occurs during the operation of the refrigerator, life and efficiency of the apparatus are adversely effected to a great extent. For example, when the phase separation of the refrigerant and the lubricating oil occurs in the part of the compressor, lubrication of the moving parts is deteriorated and seizure occurs to cause decrease of life of the apparatus to a great extent. When the phase separation occurs in the evaporator, efficiency of heat exchange is decreased because of the presence of lubricating oil of high viscosity.

Because the lubricating oil for refrigerators is used for the purpose of lubricating moving parts in refrigerators, the lubricating property is naturally important. Particularly, because the temperature in the compressor is high, the viscosity which can hold the oil film necessary for the lubrication is important. The required viscosity is different depending on the kind of the compressor used and conditions of use and it is generally preferable that viscosity (kinematic viscosity) of the lubricating oil before mixing with the refrigerant is 5 to 1000 cSt at 40° C. When the viscosity is lower than this range, oil film becomes thin to cause insufficient lubrication, and, when the viscosity is higher than this range, efficiency of the heat exchange is decreased.

Electric refrigerators have the motor and the compressor built into a single body and lubricating oil for them is required to have a high degree of electric insulating property. In general, a volume specific resistance of $10^{12} \Omega \cdot cm$ or more at 80° C. is required. When the resistance is lower than this value, possibility of leak of electricity arises.

As the refrigerant for compressor-type refrigerators, mainly dichlorodifluoromethane (referred to as Flon 12 hereinafter) has heretofore been used and, as the lubricating oil, various kinds of mineral oil and synthetic oil satisfying the required properties described above have been used. However, chlorofluorocarbons (CFC) including Flon 12 are being more rigorously restricted world-wide because they possibly cause environmental pollution such as the rupture of the ozone layer. For this reason, hydrogen-containing Flon compounds, such as hydrofluorocarbons (HFC) and hydrochlorofluorocarbons (HCFC), are attracting attention as the novel kinds of the refrigerant. The term Flon compound described above and hereinafter stands for a chlorofluorocarbon, a hydrofluorocarbon and a hydrochlorofluorocarbon in general. The hydrogen-containing fluorocarbons, particularly hydrofluorocarbons (HFC) represented by 1,1,1,2-tetrafluoroethane (referred to as Flon 134a hereinafter), are preferred as the refrigerant for compression-type refrigerators because they have little possibility of causing the rupture of the ozone layer and can replace Flon 12 with little change of the structure of refrigerators which have heretofore been used.

When a hydrogen-containing Flon compound described above, such as Flon 134a and the like, is adopted as the refrigerant for compression-type refrigerators to replace Flon 12, a lubricating oil having good compatibility with the hydrogen-containing Flon compound, such as Flon 134a and the like, and good lubricating property satisfying the requirements described above is naturally required. However, because the lubricating oils used in combination with Flon 12 heretofore do not have good compatibility with the hydrogen-containing Flon, such as Flon 134a and the like, a new lubricating oil suited for the hydrogen-containing Flon is required. When a new lubricating oil is adopted in accordance with replacement of Flon 12, it is desired that major change of the structure of the apparatus is not necessary. It is not desirable that the structure of the currently used apparatus must have major changes because of a lubricating oil.

As the lubricating oil having the compatibility with Flon 134a, for example, lubricating oils of polyoxyalkylene glycols have been known. For example, Research Disclosure No. 17463 (October, 1978), the specification of the U.S. Pat. No. 4,755,316, Japanese Patent Application Laid Open No. 1989-256594, Japanese Patent Application Laid Open No. 1989-259093, Japanese Patent Application Laid Open No. 1989-259094, Japanese Patent Application Laid Open No. 1989-271491, Japanese Patent Application Laid Open No. 1990-43290, Japanese Patent Application Laid Open No. 1990-84491, Japanese Patent Applications Laid Open No. 1990-132176 to 132178, Japanese Patent Application Laid Open No. 1990-132179, Japanese Patent Application Laid Open No. 1990-173195, Japanese Patent Applications Laid Open No. 1990-180986 to 180987, Japanese Patent Applications Laid Open No. 1990-182780 to 182781, Japanese Patent Application Laid Open No. 1990-242888, Japanese Patent Application Laid Open No. 1990-258895, Japanese Patent Application Laid Open No. 1990-269195, Japanese Patent Application Laid Open No. 1990-272097, Japanese Patent Application Laid Open No. 1990-305893, Japanese Patent Application Laid Open No. 1991-28296, Japanese Patent Application Laid Open No. 1991-33193, Japanese Patent Applications Laid Open No. 1991-103496 to 103497, Japanese Patent Application Laid Open No. 1991-50297, Japanese Patent Application Laid Open No. 1991-52995, Japanese Patent Applications Laid Open No. 1991-70794 to 70795, Japanese Patent Application Laid Open No. 1991-79696, Japanese Patent Application Laid Open No. 1991-106992, Japanese Patent Application Laid Open No. 1991-109492, Japanese Patent Application Laid Open No. 1991-

121195, Japanese Patent Application Laid Open No. 1991-205492, Japanese Patent Application Laid Open No. 1991-231992, Japanese Patent Application Laid Open No. 1991-231994, Japanese Patent Application Laid Open No. 1992-15295, Japanese Patent Application Laid Open No. 1992-39394 and Japanese Patent Applications Laid Open No. 1992-41591 to 41592 disclosed such lubricating oils. However, the lubricating oils of polyoxyalkylene glycols generally have low volume specific resistance and no example satisfying the value of $10^{12}$ Ω.cm or more at 80° C. has been disclosed yet.

As the compound having the compatibility with Flon 134a in addition to the lubricating oils of polyoxyalkylene glycols, lubricating oils of esters were disclosed in British Patent Laid Open No. 2216541, WO No. 6979 (1990), Japanese Patent Applications Laid Open No. 1990-276894, Japanese Patent Applications Laid Open No. 1991-128992, Japanese Patent Applications Laid Open No. 1991-88892, Japanese Patent Applications Laid Open No. 1991-179091, Japanese Patent Applications Laid Open No. 1991-252497, Japanese Patent Applications Laid Open No. 1991-275799, Japanese Patent Applications Laid Open No. 1992-4294, Japanese Patent Applications Laid Open No. 1992-20597 and the specification of the United States Patent No. 5021179. However, the lubricating oils of esters do not have sufficient compatibility because the phase separation occurs when viscosity of the lubricating oils is high at lower temperature even though they show good compatibility at higher temperature.

Thus, it is the real situation at present that a lubricating oil for the compression-type refrigerators having sufficiently excellent compatibility with Flon 134a, excellent stability and lubricating property and a volume specific resistance at 80° C. of $10^{12}$ Ω.cm or more has not been discovered yet. Development of such a lubricant is strongly desired.

For the applications as lubricating oils, electric insulating oils and solvents, fluidity is necessary and a polymer having a lower degree of polymerization is desired. Concerning generally known polyalkyl vinyl ethers, examples of synthesis of various kinds of alkyl polyvinyl ether are described in "Jikken Kagaku Koza", Volume 18, "Reaction of organic compounds II(A)", edited by Chemical Society of Japan (published by Maruzen). In the cases of alkyl vinyl ethers having an alkyl group of 3 or less carbon atoms among these examples, examples of the lowest molecular weight for a kind of polymer are 2545 for the polymer of methyl vinyl ether, 4000 for the polymer of ethyl vinyl ether, 4830 for the polymer of n-propyl vinyl ether and 4580 for the polymer of isopropyl vinyl ether. A polymer of methyl vinyl ether having the molecular weight of 3000 is described in Macromolecules, Volume 17, Page 2228 (1984) and a polymer of ethyl vinyl ether having the molecular weight of 2600 is described in Macromolecules, Volume 18, Page 2 (1985). However, the values of molecular weight suggest that these polymers had very low fluidity and were in the condition of semi-solid at the room temperature.

In the cases of the compounds having an alkyl group of 4 or more carbon atoms, an example in which a dimer was isolated and an example in which a polymer having molecular weight of 600 was obtained are found about butyl vinyl ether. However, polymers of alkyl vinyl ethers having an alkyl group of 4 or more carbon atoms do not satisfy the required property because they are not compatible with the hydrofluorocarbons such as Flon 134a.

As described above, polymer of a vinyl ether having an alkyl group of carbon atoms of 3 or less which has molecular weight of 1200 or less has not been known.

SUMMARY OF THE INVENTION

The present invention has an object of providing a method of producing a polyvinyl ether compound having a desired degree of polymerization reliably, safely, efficiently and industrially advantageously in the production of the polyvinyl ether compound having a wide range of applications as solvent, lubricating oil, adhesive material, resin and the like.

The present invention has another object of providing a novel polyvinyl ether compound which is favorably used as a lubricating oil for compression-type refrigerators having sufficiently excellent compatibility with hydrogen-containing Flon compounds, such as Flon 134a, excellent stability and lubricating property and a volume specific resistance at 80° C. of $10^{12}$ Ω.cm or more.

As the result of intensive studies by the present inventors to achieve the first object described above, it was discovered that the object can be achieved by polymerizing a vinyl ether compound in the presence of a Lewis acid catalyst and a specific acetal or by forming a desired acetal by addition of a material vinyl ether compound to a specific alcohol in the presence of a Lewis acid, then adding the vinyl ether compound to the acetal and polymerizing the vinyl ether compound. Furthermore, as the result of intensive studies by the present inventors to achieve the second object described above, it was discovered that the object can be achieved by a polyvinyl ether compound which is homopolymer or a copolymer of an alkyl vinyl ether having alkyl group of 1 to 3 carbon atoms, has weight average molecular weight in the range of 300 to 1200 and has a specific structure at the end. The present invention was completed on the basis of these discoveries.

Thus, the first of the present invention provides:

a method of production of a polyvinyl ether compound which comprises polymerizing a vinyl ether compound expressed by the general formula (I):

wherein $R^1$, $R^2$ and $R^3$ are a hydrogen atom or a hydrocarbon group having 1 to 8 carbon atoms, respectively, and may be the same or different from each other, $R^4$ is a bivalent hydrocarbon group having 2 to 10 carbon atoms, $R^5$ is a hydrocarbon group having 1 to 10 carbon atoms, k is a number the average of which is in the range of 0 to 10 and a plural of $R^4O$'s may be the same or different from each other when a plural of $R^4O$'s are comprised, in the presence of a Lewis acid catalyst and an acetal expressed by the general formula (II):

wherein $R^6$, $R^7$ and $R^8$ are a hydrogen atom or a hydrocarbon group having 1 to 8 carbon atoms, respectively, and may be the same or different from each other, $R^9$ and $R^{11}$ are a bivalent hydrocarbon group having 2 to 10 carbon atoms, respectively, and may the same or different from each other, $R^{10}$ and $R^{12}$ are a hydrocarbon group having 1 to 10 carbon atoms, respectively, and may be the same or different from each other, m and n are a number the average of which is in the range of 0 to 10, respectively, and may be the same or different from each other, a plural of $R^9O$'s may be the same or different from each other when a plural of $R^9O$'s are comprised and a plural of $R^{11}O$'s may be the same or different from each other when a plural of $R^{11}O$'s are comprised, and polymerized; and a method of production of a polyvinyl ether compound which comprises forming an acetal expressed by the general formula (II'):

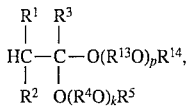

(II')

wherein $R^1$, $R^2$ and $R^3$ are a hydrogen atom or a hydrocarbon group having 1 to 8 carbon atoms, respectively, and may be the same or different from each other, $R^4$ is a bivalent hydrocarbon group having 2 to 10 carbon atoms, $R^5$ is a hydrocarbon group having 1 to 10 carbon atoms, $R^{13}$ is a bivalent hydrocarbon group having 2 to 10 carbon atoms, $R^{14}$ is a hydrocarbon group having 1 to 10 carbon atoms, k is a number the average of which is in the range of 0 to 10, respectively, a plural of $R^4O$'s may be the same or different from each other when a plural of $R^4O$'s are comprised and a plural of $R^{13}O$'s may be the same or different from each other when a plural of $R^{13}O$'s are comprised, by adding a vinyl ether monomer expressed by the general formula (I):

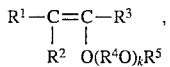

(I)

wherein $R^1$ to $R^5$ and k are the same as those described above and a plural of $R^4O$'s may be the same or different from each other when a plural of $R^4O$'s are comprised, to an alcohol expressed by the general formula (III):

(III), wherein $R^{13}$, $R^{14}$ are the same as described above, p is a number the average of which is in the range of 0 to 10 and a plural of $R^{13}O$'s may be the same or different from each other when a plural of $R^{13}O$'s are comprised, in the presence of a Lewis acid catalyst, then adding the vinyl ether monomer expressed by the general formula (I) further to the acetal and polymerizing the vinyl ether monomer.

The second of the present invention provides a polyvinyl ether compound which comprises homopolymer or a copolymer of an alkyl vinyl ether comprising the constituting unit expressed by the general formula (IV):

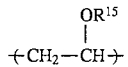

(IV)

or the general formula (IV'):

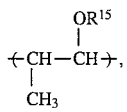

(IV')

wherein $R^{15}$ is an alkyl group having 1 to 3 carbon atoms, and having weight average molecular weight of 300 to 1200 and one end having the structure expressed by the general formula (V) or (VI):

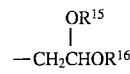

(V)

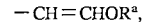

(VI)

wherein $R^{15}$ is the same as described above, $R^{16}$ is a hydrocarbon group having 1 to 8 carbon atoms and $R^a$ is either one of $R^{15}$ and $R^{16}$.

DESCRIPTION OF PREFERRED EMBODIMENTS

Figure 1:
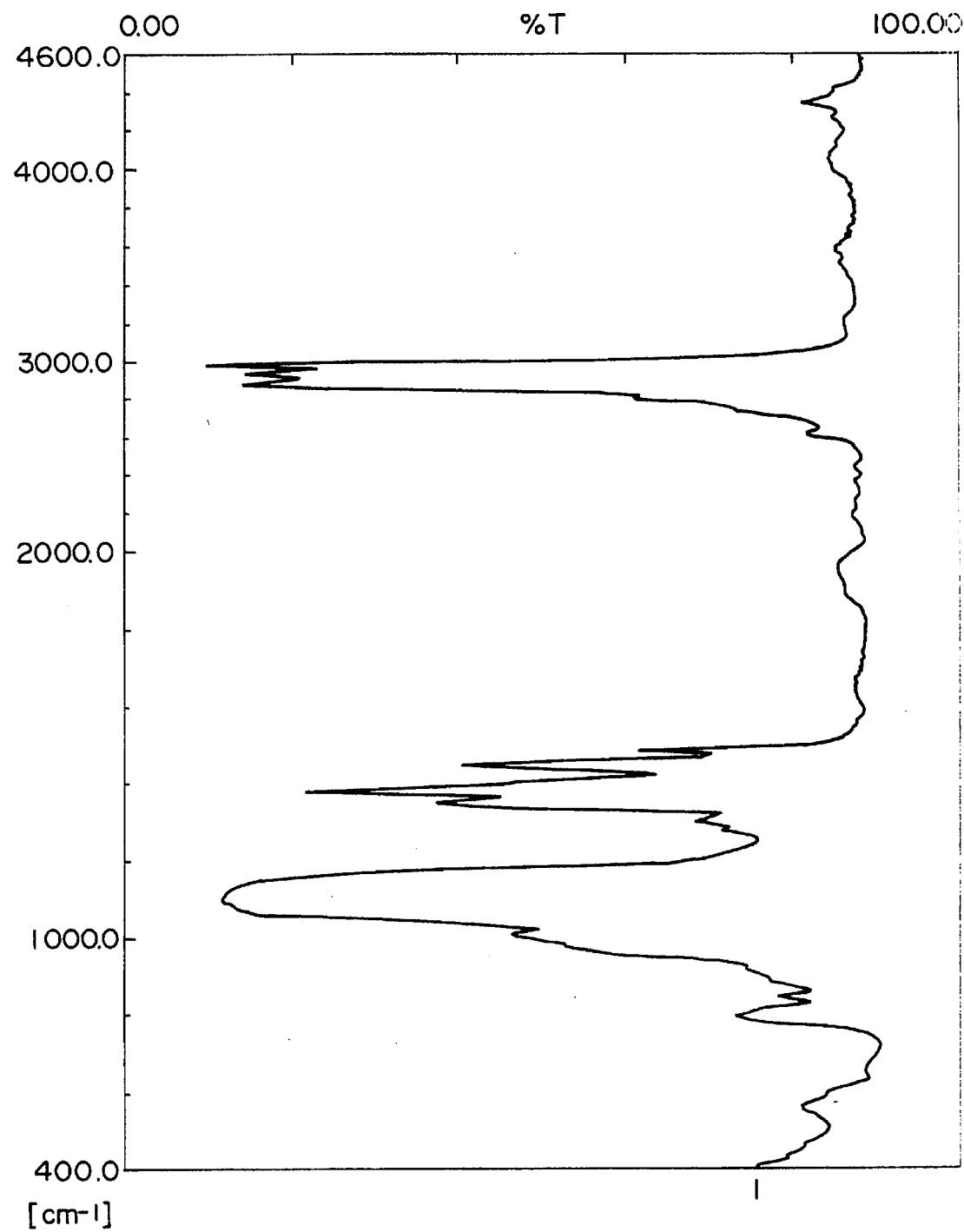
FIG. 1, FIG. 4, FIG. 7, FIG. 8, FIG. 11, FIG. 12, FIG. 15, FIG. 18 and FIG. 21 are the infrared absorption spectra of the polyvinyl ether compounds obtained in Examples 10, 11, 12, 13, 14, 15, 16, 17 and 18, respectively.

The method of production of a polyvinyl ether compound as the first object of the present invention is described first.

In the method of production of the present invention, the compound expressed by the general formula (I):

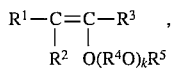

(I)

is used as the material vinyl ether compound.

$R^1$, $R^2$ and $R^3$ in the vinyl ether compound expressed by the general formula (I) are a hydrogen atom or a hydrocarbon group having 1 to 8 carbon atoms, respectively, and may be the same or different from each other. The hydrocarbon group described above is more specifically an alkyl group, such as methyl group, ethyl group, n-propyl group, isopropyl group, n-butyl group, isobutyl group, sec-butyl group, tert-butyl group, various kinds of pentyl group, various kinds of hexyl group, various kinds of heptyl group and various kinds of octyl group; a cycloalkyl group, such as cyclopentyl group, cyclohexyl group, various kinds of methylcyclohexyl group, various kinds of ethylcyclohexyl group, various kinds of dimethylcyclohexyl group and the like; an aryl group, such as phenyl group, various kinds of methylphenyl group, various kinds of ethylphenyl group and various kinds of dimethylphenyl group; or an arylalkyl group, such as benzyl group, various kinds of phenylethyl group and various kinds of methylbenzyl group. $R^1$, $R^2$ and $R^3$ are preferably a hydrogen atom or an aliphatic hydrocarbon group having 5 or less carbon atoms, respectively, and more preferably a hydrogen atom or a hydrocarbon group having 3 or less carbon atoms, respectively.

$R^4$ in the general formula (I) is a bivalent hydrocarbon group having 2 to 10 carbon atoms. The bivalent hydrocarbon group having 2 to 10 carbon atoms is more specifically a bivalent aliphatic group, such as ethylene group, phenylethylene group, 1,2-propylene group, 2-phenyl-1,2-propylene group, 1,3-propylene group, various kinds of butylene group, various kinds of pentylene group, various kinds of hexylene group, various kinds of heptylene group, various kinds of octylene group, various kinds of nonylene group and various kinds of decylene group; an alicyclic group having two bonding positions on a alicyclic hydrocarbon, such as cyclohexane, methylcyclohexane, ethylcyclohexane, dimethylcyclohexane, propylcyclohexane and the like; a bivalent aromatic hydrocarbon, such as various kinds of phenylene group, various kinds of methylphenylene group, various kinds of ethylphenylene group, various kinds of dimethylphenylene group, various kinds of naphthylene group and the like; an alkylaromatic group having one univalent bonding position on each of the alkyl part and the aromatic part of an alkylaromatic hydrocarbon, such as toluene, xylene, ethylbenzene and the like; or an alkylaromatic group having bonding positions on the parts of alkyl groups of a polyalkylaromatic hydrocarbon, such as xylene, diethylbenzene and the like. The aliphatic group having 2 to 4 carbon atoms is particularly preferable among them. A plural of $R^4O$'s may be the same or different from each other.

In the general formula (I), k shows the number of repeating and the average of k is in the range of 0 to 10 and preferably in the range of 0 to 5.

In the general formula (I), $R^5$ is a hydrocarbon group having 1 to 10 carbon atoms. The hydrocarbon group having 1 to 10 carbon atoms is more specifically an alkyl group, such as methyl group, ethyl group, n-propyl group, isopropyl group, n-butyl group, isobutyl group, sec-butyl group, tert-butyl group, various kinds of pentyl group, various kinds of hexyl group, various kinds of heptyl group, various kinds of octyl group, various kinds of nonyl group and various kinds of decyl group; a cycloalkyl group, such as cyclopentyl group, cyclohexyl group, various kinds of methylcyclohexyl group, various kinds of ethylcyclohexyl group, various kinds of propylcyclohexyl group, various kinds of dimethylcyclohexyl group and the like; an aryl group, such as phenyl group, various kinds of methylphenyl group, various kinds of ethylphenyl group, various kinds of dimethylphenyl group, various kinds of propylphenyl group, various kinds of trimethylphenyl group, various kinds of butylphenyl group, various kinds of naphthyl group and the like; or an arylalkyl group, such as benzyl group, various kinds of phenylethyl group, various kinds of methylbenzyl group, various kinds of phenylpropyl group and various kinds of butylphenyl group. A hydrocarbon having 8 or less carbon atoms is preferable among them. When k is 0, an alkyl group having 1 to 6 carbon atoms is particularly preferable and, when k is 1 or more, an alkyl group having 1 to 4 carbon atoms is particularly preferable.

Examples of the vinyl ether monomer expressed by the general formula (I) are: vinyl methyl ether, vinyl ethyl ether, vinyl n-propyl ether, vinyl isopropyl ether, vinyl n-butyl ether, vinyl isobutyl ether, vinyl sec-butyl ether, vinyl tert-butyl ether, vinyl n-pentyl ether, vinyl n-hexyl ether, vinyl 2-methoxyethyl ether, vinyl 2-ethoxyethyl ether, vinyl 2-methoxy-1-methylethyl ether, vinyl 2-methoxypropyl ether, vinyl 3,6-dioxaheptyl ether, vinyl 3,6,9-trioxadecyl ether, vinyl 1,4-dimethyl-3,6-dioxaheptyl ether, vinyl 1,4,7-trimethyl-3,6,9-trioxadecyl ether, 1-methoxypropene, 1-ethoxypropene, 1-n-propoxypropene, 1-isopropoxypropene, 1-n-butoxypropene, 1-isobutoxypropene, 1-sec-butoxypropene, 1-tert-butoxypropene, 2-methoxypropene, 2-ethoxypropene, 2-n-propoxypropene, 2-isopropoxypropene, 2-n-butoxypropene, 2-isobutoxypropene, 2-sec-butoxypropene, 2-tert-butoxypropene, 1-methoxy-1-butene, 1-ethoxy-1-butene, 1-n-propoxy-1-butene, 1-isopropoxy-1-butene, 1-n-butoxy-1-butene, 1-isobutoxy-1-butene, 1-sec-butoxy-1-butene, 1-tert-butoxy-1-butene, 2-methoxy-1-butene, 2-ethoxy-1-butene, 2-n-propoxy-1-butene, 2-isopropoxy-1-butene, 2-n-butoxy-1-butene, 2-isobutoxy-1-butene, 2-sec-butoxy-1-butene, 2-tert-butoxy-1-butene, 2-methoxy-2-butene, 2-ethoxy-2-butene, 2-n-propoxy-2-butene, 2-isopropoxy-2-butene, 2-n-butoxy-2-butene, 2-isobutoxy-2-butene, 2-sec-butoxy-2-butene, 2-tert-butoxy-2-butene and the like. These vinyl ethers can be produced by conventional methods.

As the method of polymerizing the vinyl ether compound expressed by the general formula (I), two methods are used in the present invention.

The first method is the method of polymerizing the vinyl ether compound in the presence of a Lewis acid and an acetal expressed by the general formula (II):

In the acetal compound expressed by the general formula (II) used in the method described above, $R^6$, $R^7$ and $R^8$ are a hydrogen atom or a hydrocarbon group having 1 to 8 carbon atoms, respectively, and may be the same or different from each other. Examples of the hydrocarbon group are the same as those shown as examples in the description of $R^1$ to $R^3$ in the general formula (I). $R^9$ and $R^{11}$ are a bivalent hydrocarbon group having 2 to 10 carbon atoms, respectively, and may the same or different from each other. Examples of the bivalent hydrocarbon group are the same as those shown as examples in the description of $R^4$ in the general formula (I). A plural of $R^9O$'s and $R^{11}O$'s may be the same or different from each other, respectively. Further, m and n are a number of repeating the average of which is in the range of 0 to 10, preferably in the range of 0 to 5, respectively, and may be the same or different from each other. $R^{10}$ and $R^{12}$ are a hydrocarbon group having 1 to 10 carbon atoms, respectively, and may be the same or different from each other. Examples of the hydrocarbon group having 1 to 10 carbon atoms are the same as those shown as examples in the description of $R^5$ in the general formula (I). As $R^{10}$, an alkyl group having 1 to 6 carbon atoms is particularly preferable when m is 0 and an alkyl group having 1 to 4 carbon atoms is particularly preferable when m is 1 or more. As $R^{12}$, an alkyl group having 1 to 6 carbon atoms is particularly preferable when n is 0 and an alkyl group having 1 to 4 carbon atoms is particularly preferable when n is 1 or more.

Examples of the acetal expressed by the general formula (II) are acetaldehyde dimethyl acetal, acetaldehyde diethyl acetal, acetaldehyde methyl ethyl acetal, acetaldehyde di-n-propyl acetal, acetaldehyde methyl n-propyl acetal, acetaldehyde ethyl n-propyl acetal, acetaldehyde diisopropyl acetal, acetaldehyde methyl isopropyl acetal, acetaldehyde ethyl isopropyl acetal, acetaldehyde n-propyl isopropyl acetal, acetaldehyde di-n-butyl acetal, acetaldehyde methyl n-butyl acetal, acetaldehyde ethyl n-butyl acetal, acetaldehyde n-propyl n-butyl acetal, acetaldehyde isopropyl n-butyl acetal, acetaldehyde diisobutyl acetal, acetaldehyde methyl isobutyl acetal, acetaldehyde ethyl isobutyl acetal, acetaldehyde n-propyl isobutyl acetal, acetaldehyde isopropyl isobutyl acetal, acetaldehyde n-butyl isobutyl acetal, acetaldehyde di-sec-butyl acetal, acetaldehyde methyl sec-butyl acetal, acetaldehyde ethyl sec-butyl acetal, acetaldehyde n-propyl sec-butyl acetal, acetaldehyde isopropyl sec-butyl acetal, acetaldehyde n-butyl sec-butyl acetal, acetaldehyde isobutyl sec-butyl acetal, acetaldehyde di-tert-butyl acetal, acetaldehyde methyl tert-butyl acetal, acetaldehyde ethyl tert-butyl acetal, acetaldehyde n-propyl tert-butyl acetal, acetaldehyde isopropyl tert-butyl acetal, acetaldehyde n-butyl tert-butyl acetal, acetaldehyde isobutyl tert-butyl acetal, acetaldehyde sec-butyl tert-butyl acetal, acetaldehyde di(β-methoxyethyl) acetal, acetaldehyde di(β-methoxyisopropyl) acetal, propionaldehyde dimethyl acetal, propionaldehyde diethyl acetal, propionaldehyde methyl ethyl acetal, propionaldehyde di-n-propyl acetal, propionaldehyde methyl n-propyl acetal, propionaldehyde ethyl n-propyl acetal, propionaldehyde diisopropyl acetal, propionaldehyde methyl isopropyl acetal, propionaldehyde ethyl isopropyl acetal, propionaldehyde n-propyl isopropyl acetal, propionaldehyde di-n-butyl acetal, propionaldehyde methyl n-butyl acetal, propionaldehyde ethyl n-butyl acetal, propionaldehyde n-propyl n-butyl acetal, propionaldehyde isopropyl n-butyl acetal, propionaldehyde diisobutyl acetal, propionaldehyde methyl isobutyl acetal, propionaldehyde ethyl isobutyl acetal, propionaldehyde n-propyl isobutyl acetal, propionaldehyde isopropyl isobutyl acetal, propionaldehyde n-butyl isobutyl acetal, propionaldehyde di-sec-butyl acetal, propionaldehyde methyl sec-butyl acetal, propionaldehyde ethyl sec-butyl acetal, propionaldehyde n-propyl sec-butyl acetal, propionaldehyde isopropyl sec-butyl acetal, propionaldehyde n-butyl sec-butyl acetal, propionaldehyde isobutyl sec-butyl acetal, propionaldehyde di-tert-butyl acetal, propionaldehyde methyl tert-butyl acetal, propionaldehyde ethyl tert-butyl acetal, propionaldehyde n-propyl tert-butyl acetal, propionaldehyde isopropyl tert-butyl acetal, propionaldehyde n-butyl tert-butyl acetal, propionaldehyde isobutyl tert-butyl acetal, propionaldehyde sec-butyl tert-butyl acetal, propionaldehyde di(β-methoxyethyl) acetal, propionaldehyde di(b-methoxyisopropyl) acetal, n-butyraldehyde dimethyl acetal, n-butyraldehyde diethyl acetal, n-butyraldehyde methyl ethyl acetal, n-butyraldehyde di-n-propyl acetal, n-butyraldehyde methyl n-propyl acetal, n-butyraldehyde ethyl n-propyl acetal, n-butyraldehyde diisopropyl acetal, n-butyraldehyde methyl isopropyl acetal, n-butyraldehyde ethyl isopropyl acetal, n-butyraldehyde n-propyl isopropyl acetal, n-butyraldehyde di-n-butyl acetal, n-butyraldehyde methyl n-butyl acetal, n-butyraldehyde ethyl n-butyl acetal, n-butyraldehyde n-propyl n-butyl acetal, n-butyraldehyde isopropyl n-butyl acetal, n-butyraldehyde diisobutyl acetal, n-butyraldehyde methyl isobutyl acetal, n-butyraldehyde ethyl isobutyl acetal, n-butyraldehyde n-propyl isobutyl acetal, n-butyraldehyde isopropyl isobutyl acetal, n-butyraldehyde n-butyl isobutyl acetal, n-butyraldehyde di-sec-butyl acetal, n-butyraldehyde methyl sec-butyl acetal, n-butyraldehyde ethyl sec-butyl acetal, n-butyraldehyde n-propyl sec-butyl acetal, n-butyraldehyde isopropyl sec-butyl acetal, n-butyraldehyde n-butyl sec-butyl acetal, n-butyraldehyde isobutyl sec-butyl acetal, n-butyraldehyde di-tert-butyl acetal, n-butyraldehyde methyl tert-butyl acetal, n-butyraldehyde ethyl tert-butyl acetal, n-butyraldehyde n-propyl tert-butyl acetal, n-butyraldehyde isopropyl tert-butyl acetal, n-butyraldehyde n-butyl tert-butyl acetal, n-butyraldehyde isobutyl tert-butyl acetal, n-butyraldehyde sec-butyl tert-butyl acetal, n-butyraldehyde di(β-methoxyethyl) acetal, n-butyraldehyde di(β-methoxyisopropyl) acetal and the like.

The second method is the method in which an acetal having the general formula (II'):

(II')

is formed by adding the vinyl ether monomer expressed by the general formula (I) to an alcohol expressed by the general formula (III):

$$R^{14}(OR^{13})_pOH \qquad (III),$$

($R^1$ to $R^5$, $R^{13}$, $R^{14}$, k and p in the general formulae are the same as described above) in the presence of a Lewis acid catalyst and then the vinyl ether monomer expressed by the general formula (I) is added further to the acetal and polymerized.

In the alcohol expressed by the general formula (III), $R^{13}$ is a bivalent hydrocarbon group having 2 to 10 carbon atoms and examples of the bivalent hydrocarbon group are the same as those shown as examples in the description of $R^4$ in the general formula (I). A plural of $R^{13}O$'s may be the same or different from each other. Further, p is the number of repeating and the average is in the range of 0 to 10 and preferably in the range of 0 to 5. $R^{14}$ is a hydrocarbon group having 1 to 10 carbon atoms and examples of the hydrocarbon group are the same as those shown as examples in the description of $R^5$ in the general formula (I). As $R^{14}$, an alkyl group having 1 to 6 carbon atoms is particularly preferable when p is 0 and an alkyl group having 1 to 4 carbon atoms is particularly preferable when p is 1 or more.

Examples of the alcohol expressed by the general formula (III) are: saturated aliphatic alcohols, such as methanol, ethanol, propanol, isopropanol, butanol, isobutanol, sec-butanol, tert-butanol, various kinds of pentanol, various kinds of hexanol, various kinds of octanol and the like; unsaturated aliphatic alcohols having 3 to 10 carbon atoms, such as allyl alcohol and the like; alcohols having 3 to 10 carbon atoms and containing oxygen bonded as the ether bond, such as ethylene glycol monoalkyl ethers, ethylene glycol monoaryl ethers, propylene glycol monoalkyl ethers, propylene glycol monoaryl ethers, polyethylene glycol monoalkyl ethers, polyethylene glycol monoaryl ethers, polypropylene glycol monoalkyl ethers, polypropylene glycol monoaryl ethers, 1,3-dimethoxy-2-propanol, 1-ethoxy-3-methoxy-2-propanol, 1,3-diethoxy-2-propanol and the like; and the like compounds.

Examples of the Lewis acid catalyst used in the first method and in the second method described above, are boron trifluoride and complexes thereof, aluminum chloride, ferric chloride, zinc chloride, tin chlorides and the like. Among them, boron trifluoride and complexes thereof are particularly preferable.

To the initiated end of the polymer, hydrogen is attached when an alcohol is used as the case in the second method and, when the acetal is used as the case in the first method, the group formed by elimination of one of the alkoxy groups from the used acetal is attached. On the other hand, an acetal group or an olefin group is formed at the terminated end of the polymer.

The polymerization of the vinyl ether monomer expressed by the general formula (I) can be performed at a temperature generally in the range of −80° to +150° C., preferably in the range of 0° to 100° C., although the temperature is varied depending on kinds of the materials and the initiator. When an acetal is utilized, generation of heat by the heat of polymerization is observed without an induction period and, when an alcohol is utilized, generation of heat by the heat of polymerization is observed without an induction period after the formation of the acetal. Thus, control of the temperature during the reaction can be easily performed by adding the vinyl ether monomer with a speed which balances with the ability of the apparatus to eliminate the heat. The polymerization is finished generally in the time of about 10 seconds to about 10 hours after the start of the reaction.

For adjusting molecular weight in the polymerization reaction, a polymer having lower average molecular weight is obtained by increasing amount of the acetal expressed by the general formula (II) or the alcohol expressed by the formula (III) relative to the amount of the vinyl ether compound expressed by the formula (I).

The polymerization can be performed without a solvent but a solvent may be used when the solvent is stable in the reaction condition. The kind of the solvent is not particularly limited. Preferable examples of the solvent are hydrocarbon solvents, such as hexane, benzene, toluene, various kinds of xylene and the like, and ether solvents, such as ethyl ether, 1,2-dimethoxyethane, tetrahydrofuran and the like. The polymerization reaction can be terminated by addition of an alkali.

After the polymerization has been conducted as described above, the desired polyvinyl ether compound can be obtained after separation and purification by the generally used methods according to necessity.

The novel polyvinyl ether compound as the second object of the present invention is described in the following.

The polyvinyl ether compound of the present invention comprises homopolymer or a copolymer of an alkyl vinyl ether having an alkyl group of 1 to 3 carbon atoms. It is necessary that the weight average molecular weight of the polymer is in the range of 300 to 1200 and preferably in the range of 400 to 1000. The ratio of weight average molecular weight and number average molecular weight is generally in the range of 1.05 to 1.50 and preferably in the range of 1.06 to 1.40.

The polyvinyl ether compound of the present invention can be produced by polymerization of the corresponding vinyl ether monomer. Examples of the vinyl ether monomer are vinyl methyl ether, vinyl ethyl ether, vinyl n-propyl ether and vinyl isopropyl ether. The vinyl ether monomer can be used singly or as a combination of two or more kinds.

As the method of polymerization of the vinyl ether compound described above, radical polymerization, cationic polymerization and irradiation polymerization can be adopted as described in "Gosei Kobunshi III", edited by Shunsuke Murahashi, Minoru Imoto and Hisaya Tani (published by Asakura Shoten). A polymer having the desired viscosity can be obtained by polymerization according to the method described in the following.

For the initiation of the polymerization, a combination of a Brønsted acid, a Lewis acid or an organometallic compound and an alcohol or an acetal can be used. Examples of the Brønsted acid are hydrofluoric acid, hydrochloric acid, hydrobromic acid, hydriodic acid, nitric acid, sulfuric acid, trichloroacetic acid, trifluoroacetic acid and the like. As the Lewis acid, the compounds shown as examples in the description of the method of production of the polyvinyl ether compound as the first object of the present invention can be used. Particularly, boron trifluoride and complexes thereof are preferred.

Examples of the alcohol are methanol, ethanol, propanol, isopropanol, butanol, isobutanol, sec-butanol, tertobutanol, various kinds of pentanol, various kinds of hexanol and the like. Among these compounds, alcohols having 3 or less carbon atoms are preferable. Particularly, methanol and ethanol are preferred.

As the acetals, the same compounds as those shown as examples in the description of the acetal expressed by the general formula (II) in the method of production of polyvinyl ether compound as the first object of the present invention can be mentioned.

The polyvinyl ether compound of the present invention thus obtained comprises homopolymer or a copolymer of an alkyl vinyl ether comprising one kind or two kinds or more of the constituting units expressed by the formula (IV):

$$\begin{array}{c} OR^{15} \\ | \\ \text{--}(CH_2\text{--}CH)\text{--} \end{array} \quad (IV)$$

or the formula (IV'):

$$\begin{array}{c} OR^{15} \\ | \\ \text{--}(CH\text{--}CH)\text{--}, \\ | \\ CH_3 \end{array} \quad (IV')$$

wherein $R^{15}$ is an alkyl group having 1 to 3 carbon atoms, and one end having the structure expressed by the formula (V) or (VI):

$$\begin{array}{c} OR^{15} \\ | \\ \text{--}CH_2CHOR^{16} \end{array} \quad (V)$$

$$\text{--}CH=CHOR^a, \quad (VI)$$

wherein $R^{15}$ is the same as those in the formula (I), $R^{16}$ is a hydrocarbon group having 1 to 8 carbon atoms and $R^a$ is either one of $R^1$ and $R^2$.

In the formula (V), $R^{16}$ is derived from the residual group formed by eliminating the hydroxyl group from the alcohol or from the residual group formed by eliminating the oxygen atom from the alkoxy group in the acetal, both used for the initiation of the polymerization.

To the initiated end, a hydrogen is attached when the alcohol is used and the residual group formed by eliminating one of the alkoxy groups from the acetal is attached when the acetal is used. To the terminated end, the acetal group expressed by the formula (V) described above or the olefin group expressed by the formula (VI) described above is attached.

The homopolymer or the copolymer of the alkyl vinyl ether may comprise the terminated end expressed by the formula (V) alone, the terminated end expressed by the formula (VI) alone or the terminated end having a mixed structure of them.

The polymerization can be performed at a temperature in the range of −80° to 150° C., preferably in the range of 0° to 100° C. although the temperature varies depending on the kinds of the materials and the catalyst or the initiator. The polymerization reaction is finished generally in a time of about 10 seconds to about 10 hours after the start of the reaction.

For adjusting the molecular weight in the polymerization reaction, the molecular weight of the polymer is decreased by the increased amount of the alcohol described above or the acetal described above.

The polymerization is conducted generally in the presence of a solvent. The solvent is not particularly limited so long as it dissolves necessary amount of the reacting materials and is inert to the reaction. For example, hydrocarbon solvents, such as hexane, benzene, toluene and the like and ether solvents, such as ethyl ether, 1,2-dimethoxyethane, tetrahydrofuran and the like are preferably used. The polymerization can be terminated by adding an alkali.

According to the method of production of the present invention, the polyvinyl ether with the desired degree of polymerization can be produced reliably, safely, efficiently and industrially advantageously in the production of the polyvinyl ether compound having a wide range of applications, such as solvents, lubricating oils, adhesive materials, resin and the like.

Further, the polyvinyl ether compound of the present invention is homopolymer or a copolymer of an alkyl vinyl ether having alkyl group of 1 to 3 carbon atoms and having a relatively low molecular weight and a narrower dispersion.

The polyvinyl ether compound has excellent compatibility particularly with hydrogen-containing Flons such as Flon 134a, excellent stability and lubricating property and a volume specific resistance at 80° C. of $10^{12}$ Ω.cm or more and is favorably used as the lubricating oil for compression-type refrigerators.

The polyvinyl ether compound is useful also as an electric insulating oil, an organic solvent, a surface active agent and the like.

The present invention is described with reference to examples in more detail in the following. However, the present invention is not limited by the examples.

The methods of measurements of kinematic viscosity, compatibility with Flon, volume specific resistance and average molecular weights are shown in the following.

(1) Kinematic viscosity

Kinematic viscosity was measured according to the method of Japanese Industrial Standard K-2283 (1983) by using a glass capillary viscometer.

(2) Compatibility test

A sample of a specified amount adjusted to make 5 weight % or 10 weight % based on Flon 134a (1,1,1,2-tetrafluoroethane) was charged into a pressure resistant glass ampoule and the ampoule was connected to the vacuum line and the line for Flon 134a gas. The ampoule was degassed in vacuum at the room temperature, cooled with liquid nitrogen and a specified amount of Flon 134a was taken into the ampoule. The ampoule was then sealed and the temperature at which the phase separation starts was measured by slowly cooling the sample from the room temperature to −60° C. in a thermostatted vessel for the measurement of the compatibility at the lower temperature side and by slowly heating the sample from the room temperature to +80° C. in a thermostatted vessel for the measurement of the compatibility at the higher temperature side. A lower temperature of the phase separation is preferable in the measurement at the lower temperature side and a higher temperature of the phase separation is preferable in the measurement at the higher temperature side.

(3) Volume specific resistance

A sample was dried under the reduced pressure (0.3 to 0.8 mmHg) at 100° C. for 1 hour and then charged into a liquid cell for the measurement of volume specific resistance which is placed into a thermostatted vessel at 80° C. After the sample was kept in the thermostatted vessel at 80° C. for 40 minutes, the volume specific resistance was measured at the added electric pressure of 250 V by using an ultrainsulation meter R8340 produced by Advantest Co.

(4) Average molecular weights (Examples 10 to 18)

Weight average molecular weight and number average molecular weight were measured by using the apparatus and in the conditions shown in the following and dispersion (weight average molecular weight/number average molecular weight) was obtained from these results.

| | |
|---|---|
| Apparatus: | a product of Nippon Bunko Kogyo Co., Ltd., 880-PU (pump). Shodex RI SE-61 (detector) |
| Column: | TSK H8 + G2000 H8 + G1000 H8 |
| Temperature: | the room temperature |
| Solvent: | THF (tetrahydrofuran) |
| Speed of elution: | 1.4 ml/minute |
| Standard substance: | polyethylene glycol |

EXAMPLE 1

Into a 5 liter glass flask equipped with a dropping funnel, a cooler and a stirrer, 1000 g of toluene, 195 g of ethanol and 5.0 g of boron trifluoride diethyl etherate were charged. Temperature of the solution was 14° C. To the solution, 102 g of ethyl vinyl ether was added. As the reaction started, the temperature of the reaction solution increased by the heat of reaction and the reaction solution was kept stirring while it was cooled with an ice water bath. (The temperature of the solution reached to the maximum of 21° C. 3 minutes after the addition of ethyl vinyl ether. The reaction was conducted by cooling with the ice water bath in the following procedures.) When the temperature decreased to 15° C., 102 g of ethyl vinyl ether was added again. The generation of heat was observed again and the temperature increased. When the temperature decreased to 15° C., 102 g of ethyl vinyl ether was added further. The generation of heat was observed again and the temperature of the solution was also increased. When decrease of the temperature of the solution was observed, ethyl vinyl ether was dropped and the generation of heat was observed immediately in response with the addition. Thereafter, 2700 g of ethyl vinyl ether was dropped into the solution at about constant speed (about 20 cc/minute) in such a manner that the temperature of the reaction solution was kept constant at 25° C. After finishing the dropping, the reaction mixture was transferred to a washing vessel and washed with 1000 ml of a 3 weight % aqueous solution of sodium hydroxide 3 times and then with 1000 ml of water 3 times. The solvent and materials having lower boiling points were removed under the reduced pressure by using a rotary evaporator to obtain 3040 g of the product. The product had color of light yellow.

The product had the kinematic viscosity of 44.3 cSt at 40° C. and 5.90 cSt at 100° C.

EXAMPLE 2

Into a 500 ml glass flask equipped with a dropping funnel, a cooler and a stirrer, 36 g of acetaldehyde diethyl acetal, 80 g of toluene and 0.36 g of boron trifluoride diethyl etherate were charged. Temperature of the solution was 15° C. When ethyl vinyl ether was dropped into the solution, generation of heat was observed immediately in response with the addition of ethyl vinyl ether and 256 g of ethyl vinyl ether was dropped at about constant speed (about 5 cc/minute) in such a manner that the temperature of the reaction solution was kept constant at 25° C. while the reaction solution was cooled with an ice water bath. After finishing the dropping, the reaction mixture was transferred to a washing vessel and washed with 100 ml of a 3 weight % aqueous solution of sodium hydroxide 3 times and then with 100 ml of water 3 times. The solvent and materials having lower boiling points were removed under the reduced pressure by using a rotary evaporator to obtain 277 g of the product. The product had color of light yellow.

The product had the kinematic viscosity of 130.7 cSt at 40° C. and 11.8 cSt at 100° C.

EXAMPLE 3

Into a 500 ml glass flask equipped with a dropping funnel, a cooler and a stirrer, 18 g of acetaldehyde diethyl acetal, 80 g of toluene and 0.18 g of boron trifluoride diethyl etherate were charged. The temperature of the solution was 15° C. When ethyl vinyl ether was dropped into the solution, generation of heat was observed immediately in response with the addition of ethyl vinyl ether and 256 g of ethyl vinyl ether was dropped at about constant speed (about 5 cc/minute) in such a manner that the temperature of the reaction solution was kept constant at 25° C. while the reaction solution was cooled with an ice water bath. After finishing the dropping, the reaction mixture was transferred to a washing vessel and washed with 100 ml of a 3 weight % aqueous solution of sodium hydroxide 3 times and then with 100 ml of water 3 times. The solvent and materials having lower boiling points were removed under the reduced pressure by using a rotary evaporator to obtain 261 g of the product. The product had color of light yellow.

The product had the kinematic viscosity of 993.1 cSt at 40° C. and 44.7 cSt at 100° C.

EXAMPLE 4

Into a 500 ml glass flask equipped with a dropping funnel, a cooler and a stirrer, 9 g of acetaldehyde diethyl acetal, 80 g of toluene and 0.09 g of boron trifluoride diethyl etherate were charged. Temperature of the solution was 15° C. When ethyl vinyl ether was dropped into the solution, generation of heat was observed immediately in response with the addition of ethyl vinyl ether and 256 g of ethyl vinyl ether was dropped at about constant speed (about 5 cc/minute) in such a manner that the temperature of the reaction solution was kept constant at 25° C. while the reaction solution was cooled with an ice water bath. After finishing the dropping, the reaction mixture was transferred to a washing vessel and washed with 100 ml of a 3 weight % aqueous solution of sodium hydroxide 3 times and then with 100 ml of water 3 times. The solvent and materials having lower boiling points were removed under the reduced pressure by using a rotary evaporator to obtain 255 g of the product. The product had color of light yellow.

The product had the kinematic viscosity of 9356 cSt at 40° C. and 225.5 cSt at 100° C.

EXAMPLE 5

Into a 500 ml glass flask equipped with a dropping funnel, a cooler and a stirrer, 4 g of acetaldehyde diethyl acetal, 80 g of toluene and 0.04 g of boron trifluoride diethyl etherate were charged. The temperature of the solution was 15° C. When ethyl vinyl ether was dropped into the solution, generation of heat was observed immediately in response with the addition of ethyl vinyl ether and 256 g of ethyl vinyl ether was dropped at about constant speed (about 5 cc/minute) in such a manner that the temperature of the reaction solution was kept constant at 25° C. while the reaction solution was cooled with an ice water bath. After finishing the dropping, the reaction mixture was transferred to a washing vessel and washed with 100 ml of a 3 weight % aqueous solution of sodium hydroxide 3 times and then with 100 ml of water 3 times. The solvent and materials having lower boiling points were removed under the reduced pressure by using a rotary evaporator to obtain 252 g of the product. The product had color of light yellow.

The product had the weight average molecular weight of 2079 and the number average molecular weight of 6750.

The average molecular weights were obtained by the GPC measurement in the following condition (This condition was used in this Example only.):

| Apparatus: | a product of Nippon Bunko Co., Ltd., 880-PU (pump) SHODEX RI SE-61 (detector) |
|---|---|
| Column: | TSK HM + GMH 6 × 2+G2000H8 |
| Temperature: | the room temperature |
| Solvent: | THF |
| Speed of elution: | 1.4 ml/minute |
| Standard substance: | polystyrene |

EXAMPLE 6

Into a 500 ml glass flask equipped with a dropping funnel, a cooler and a stirrer, 16 g of acetaldehyde diethyl acetal, 80 g of toluene and 0.16 g of boron trifluoride diethyl etherate were charged. Temperature of the solution was 15° C. When ethyl vinyl ether was dropped into the solution, generation of heat was observed immediately in response with the addition of ethyl vinyl ether and 256 g of ethyl vinyl ether was dropped at about constant speed (about 5 cc/minute) in such a manner that the temperature of the reaction solution was kept constant at 25° C. while the reaction solution was cooled with an ice water bath. After finishing the dropping, the reaction mixture was transferred to a washing vessel and washed with 100 ml of a 3 weight % aqueous solution of sodium hydroxide 3 times and then with 100 ml of water 3 times. The solvent and materials having lower boiling points were removed under the reduced pressure by using a rotary evaporator to obtain 262 g of the product. The product had color of light yellow.

The product had the kinematic viscosity of 1746 cSt at 40° C. and 64.6 cSt at 100° C.

EXAMPLE 7

Into a 500 ml glass flask equipped with a dropping funnel, a cooler and a stirrer, 15 g of acetaldehyde diethyl acetal, 80 g of toluene and 0.15 g of boron trifluoride diethyl etherate were charged. Temperature of the solution was 15° C. When ethyl vinyl ether was dropped into the solution, generation of heat was observed immediately in response with the addition of ethyl vinyl ether and 256 g of ethyl vinyl ether was dropped at about constant speed (about 5 cc/minute) in such a manner that the temperature of the reaction solution was kept constant at 25° C. while the reaction solution was cooled with an ice water bath. After finishing the dropping, the reaction mixture was transferred to a washing vessel and washed with 100 ml of a 3 weight % aqueous solution of sodium hydroxide 3 times and then with 100 ml of water 3 times. The solvent and materials having lower boiling points were removed under the reduced pressure by using a rotary evaporator to obtain 260 g of the product. The product had color of light yellow.

The product had the kinematic viscosity of 1903 cSt at 40° C. and 68.1 cSt at 100° C.

EXAMPLE 8

Into a 500 ml glass flask equipped with a dropping funnel, a cooler and a stirrer, 4 g of acetaldehyde diethyl acetal, 30 g of toluene and 0.4 g of $FeCl_3.6H_2O$ were charged. Temperature of the solution was 10° C. When ethyl vinyl ether was dropped into the solution, generation of heat was observed immediately in response with the addition of ethyl vinyl ether and 30 g of ethyl vinyl ether was dropped at about constant speed in such a manner that the temperature of the reaction solution was kept constant at 10° C. while the reaction solution was cooled with an ice water bath. After finishing the dropping, the reaction mixture was transferred to a washing vessel and washed with 15 ml of a 3 weight % aqueous solution of sodium hydroxide 3 times and then with 15 ml of water 3 times. The solvent and materials having lower boiling points were removed under the reduced pressure by using a rotary evaporator to obtain 30.6 g of the product. The product had color of dark yellow.

The product had the kinematic viscosity of 21.86 cSt at 40° C. and 3.94 cSt at 100° C.

EXAMPLE 9

Into a 500 ml glass flask equipped with a dropping funnel, a cooler and a stirrer, 3 g of acetaldehyde diethyl acetal, 30 g of toluene and 0.18 g of FeCl$_3$ were charged. Temperature of the solution was 15° C. When ethyl vinyl ether was dropped into the solution, generation of heat was observed immediately in response with the addition of ethyl vinyl ether and 30 g of ethyl vinyl ether was dropped at about constant speed in such a manner that the temperature of the reaction solution was kept constant at 30° C. while the reaction solution was cooled with an ice water bath. After finishing the dropping, the reaction mixture was transferred to a washing vessel and washed with 15 ml of a 3 weight % aqueous solution of sodium hydroxide 3 times and then with 15 ml of water 3 times. The solvent and materials having lower boiling points were removed under the reduced pressure by using a rotary evaporator to obtain 29.4 g of the product. The product had color of dark yellow.

The product had the kinematic viscosity of 326.7 cSt at 40° C. and 25.69 cSt at 100° C.

EXAMPLE 10

Into a 5 liter glass flask equipped with a dropping funnel, a cooler and a stirrer, 1000 g of toluene, 234 g of ethanol and 6.0 g of boron trifluoride diethyl etherate were charged. Into a dropping funnel, 2526 g of ethyl vinyl ether was charged and dropped in 3 hours and 20 minutes. During this period, increase of the temperature of the reaction solution by the heat of reaction was observed and the temperature was kept at about 25° C. by cooling with an ice water bath. Until the amount of the monomer reached the equivalent amount to ethanol, the monomer was dropped slowly because there was an induction period for the heat generation. After finishing the dropping, the solution was further stirred for 5 minutes. The reaction mixture was transferred to a washing vessel and washed with 870 ml of a 5 weight % aqueous solution of sodium hydroxide 3 times and then with 870 ml of water 3 times. The solvent and unreacted materials were removed under the reduced pressure by using a rotary evaporator to obtain 2622 g of the polymer of ethyl vinyl ether. The product had color of light yellow.

Kinematic viscosity, average molecular weights, dispersion of molecular weight, compatibility with Flon and volume specific resistance of the polymer of ethyl vinyl ether obtained in the above were measured. The results are shown in Table 1.

Figure 2:
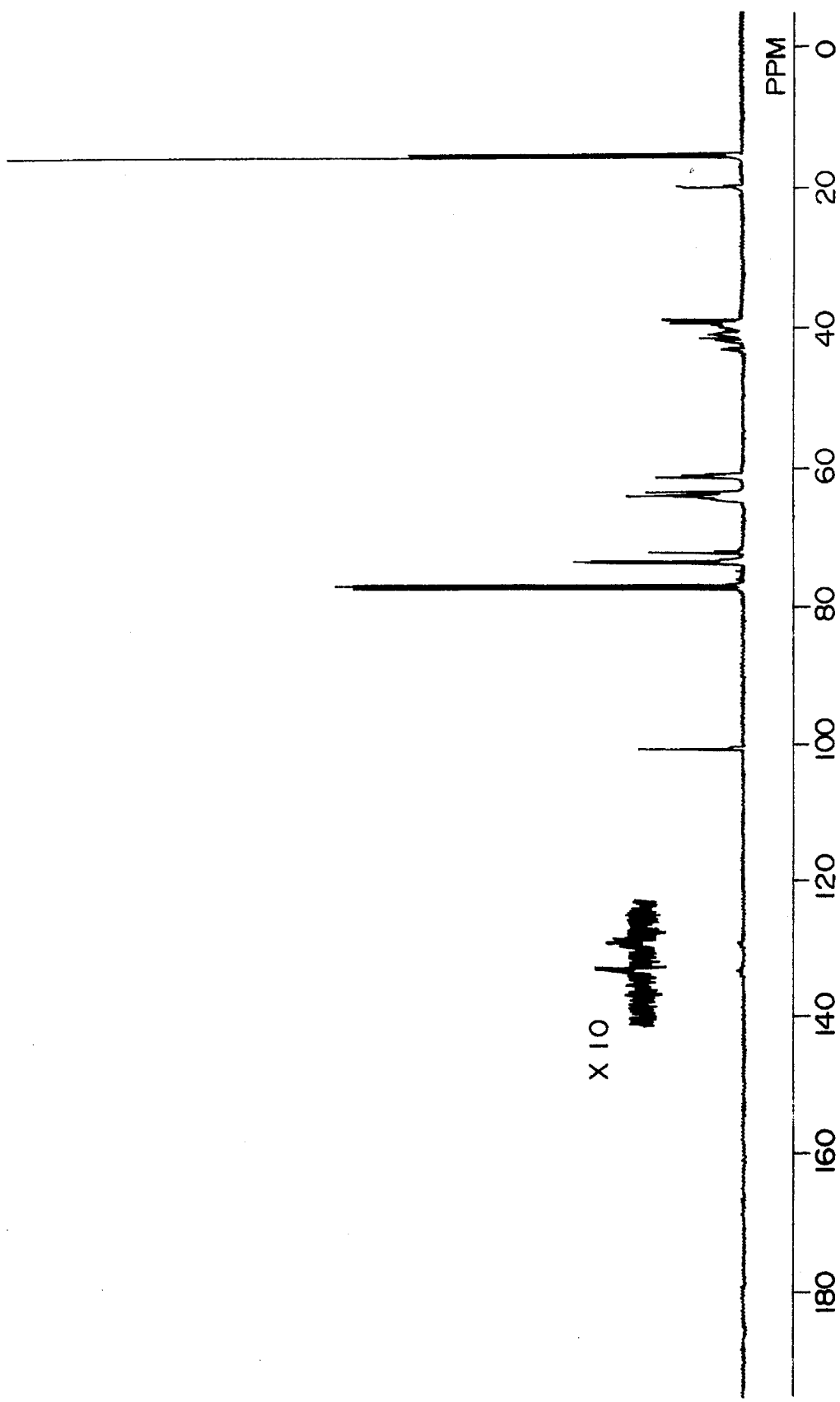
FIG. 2, FIG. 5, FIG. 9, FIG. 13, FIG. 16, FIG. 19 and FIG. 22 are the $^{13}$C-NMR charts of the polyvinyl ether compounds obtained in Examples 10, 11, 13, 15, 16, 17 and 18, respectively.
Figure 3:
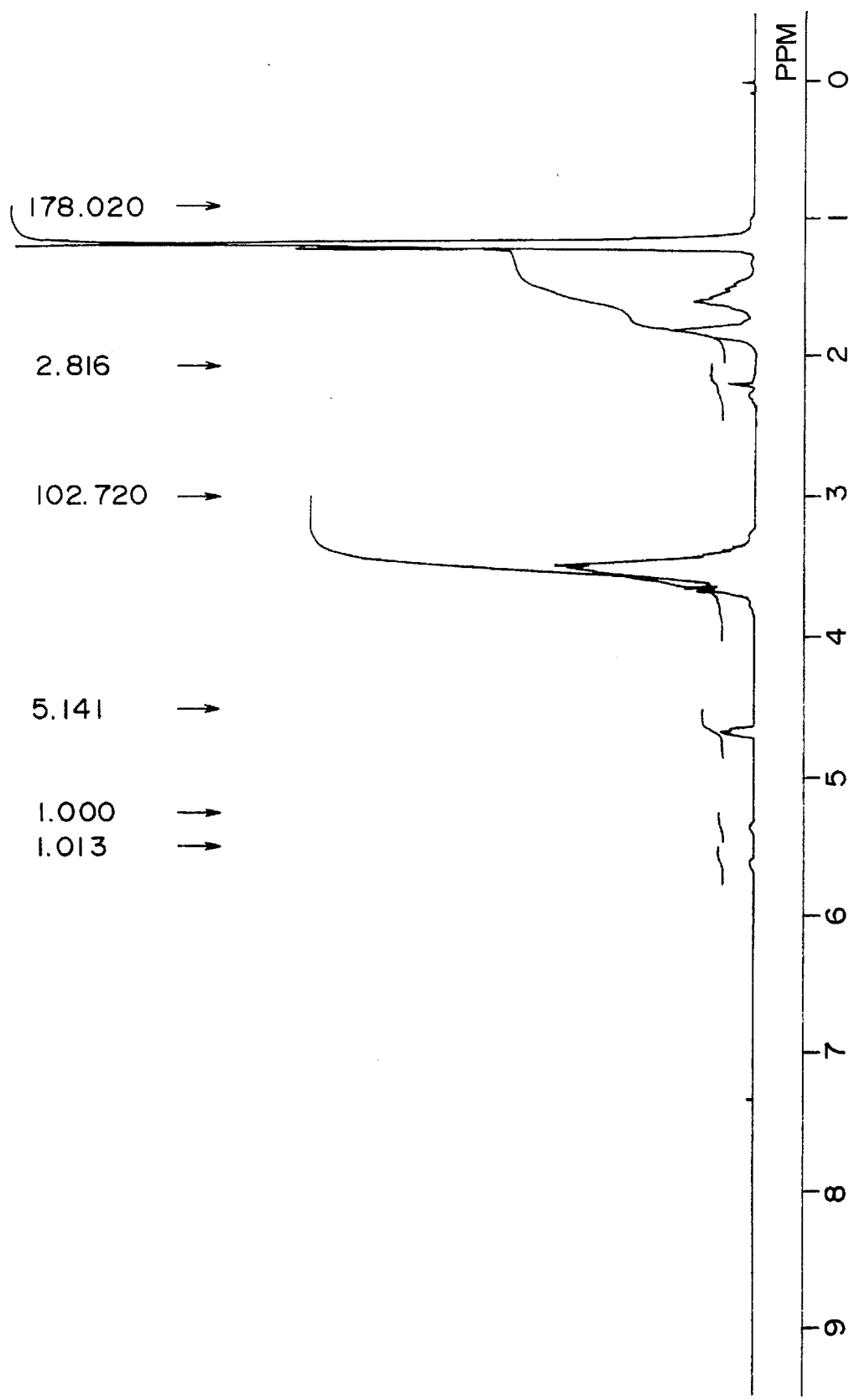
FIG. 3, FIG. 6, FIG. 10, FIG. 14, FIG. 17, FIG. 20 and FIG. 23 are the $^1$H-NMR charts of the polyvinyl ether compounds obtained in Examples 10, 11, 13, 15, 16, 17 and 18, respectively.

The infrared absorption spectrum is shown in FIG. 1, the $^{13}$C-NMR chart is shown in FIG. 2 and the $^1$H-NMR chart is show in FIG. 3.

In FIG. 2, the peaks at 101 ppm, 129 ppm and 134 ppm are peaks derived from the carbon atom underlined in the following formulae, respectively:

—CH$_2$—C̲H(OC$_2$H$_5$)$_2$

—C̲H=CH—OC$_2$H$_5$

—CH=C̲H—OC$_2$H$_5$.

In FIG. 3, the peaks at 4.7 ppm, 5.35 ppm and 5.6 ppm are peaks derived from the hydrogen atom underlined in the following formulae, respectively:

—CH$_2$—C̲H(OC$_2$H$_5$)$_2$

—CH=CH—OC$_2$H$_5$

—CH=C̲H—OC$_2$H$_5$.

Therefore, the end of the compound was a mixture of the formula (V) and the formula (VI) and the ratio of the numbers of molecule obtained from the ratio of proton was: (V):(VI)=5.1:1.

EXAMPLE 11

Into a 5 liter glass flask equipped with a dropping funnel, a cooler and a stirrer, 1000 g of toluene, 195 g of ethanol and 5.0 g of boron trifluoride diethyl etherate were charged. Into a dropping funnel, 3005 g of ethyl vinyl ether was charged and dropped in 3 hours and 50 minutes. During this period, increase of the temperature of the reaction solution by the heat of reaction was observed and the temperature was kept at about 25° C. by cooling with an ice water bath. Until the amount of the monomer reached the equivalent amount to ethanol, the monomer was dropped slowly because there was an induction period for the heat generation. After finishing the dropping, the solution was further stirred for 5 minutes. The reaction mixture was transferred to a washing vessel and washed with 1000 ml of a 5 weight % aqueous solution of sodium hydroxide 3 times and then with 1000 ml of water 3 times. The solvent and unreacted materials were removed under the reduced pressure by using a rotary evaporator to obtain 3008 g of the polymer of ethyl vinyl ether. The product had color of light yellow.

Kinematic viscosity, average molecular weights, dispersion of molecular weight, compatibility with Flon and volume specific resistance of the polymer of ethyl vinyl ether obtained in the above were measured. The results are shown in Table 1.

Figure 4:
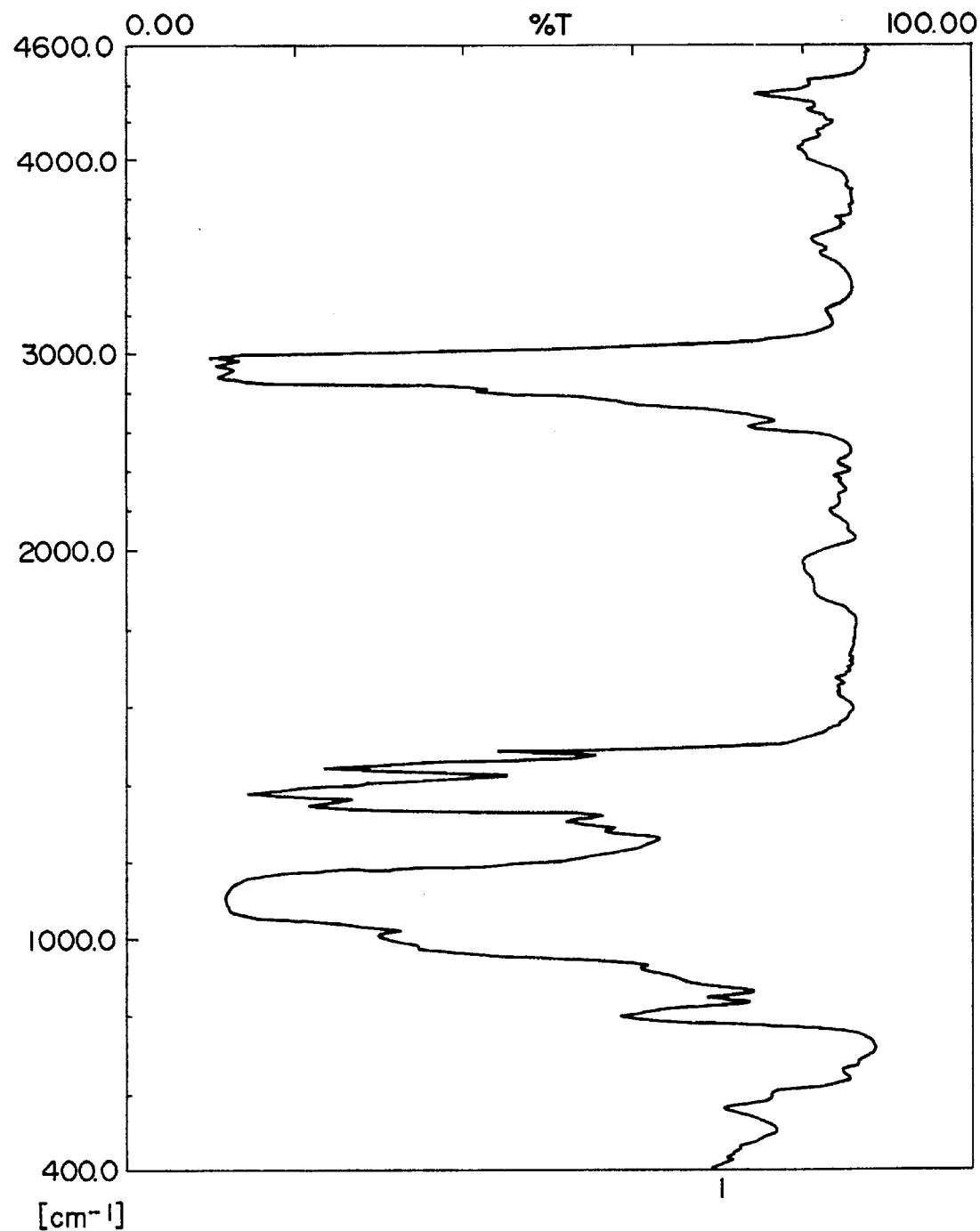
Figure 5:
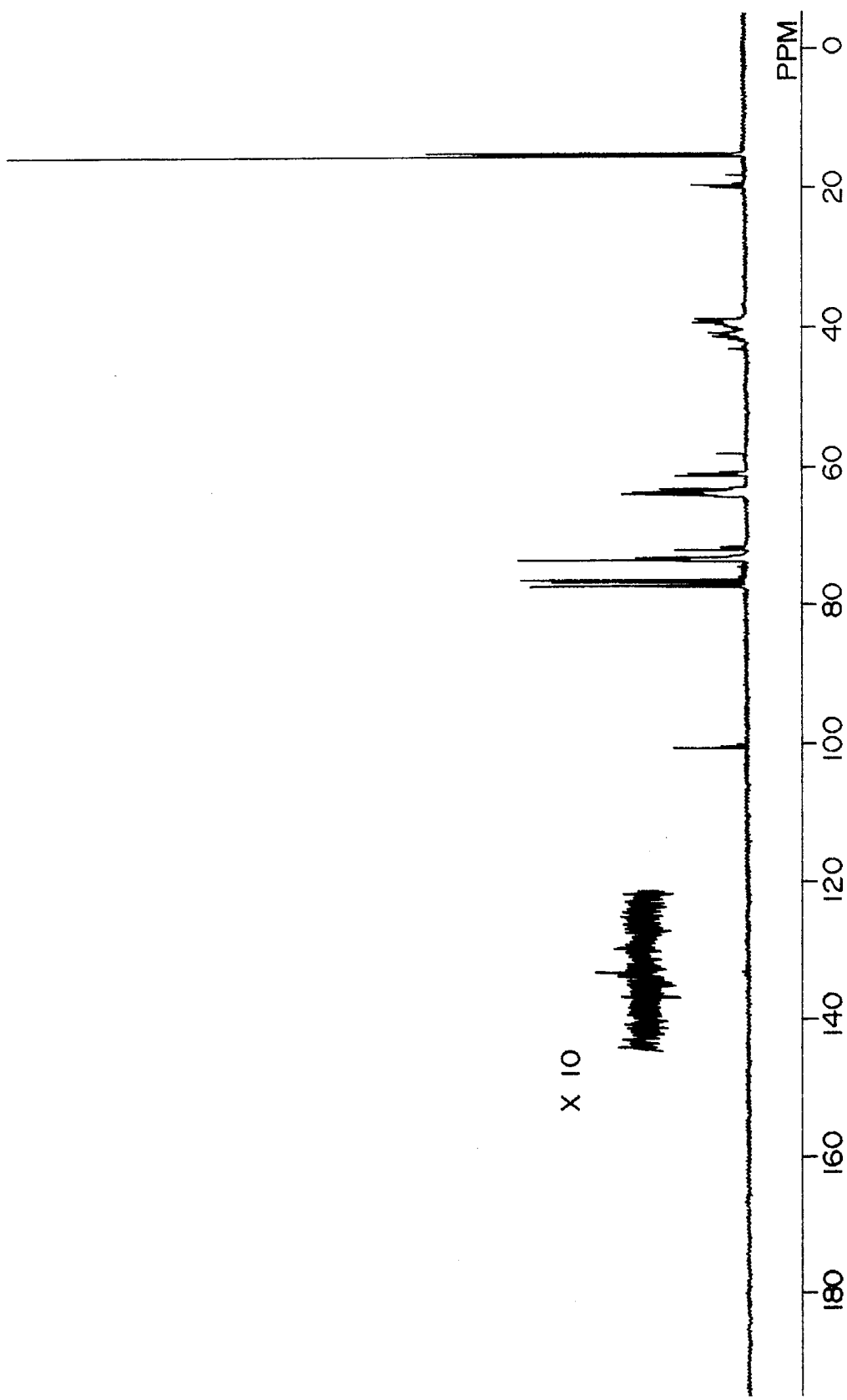
Figure 6:
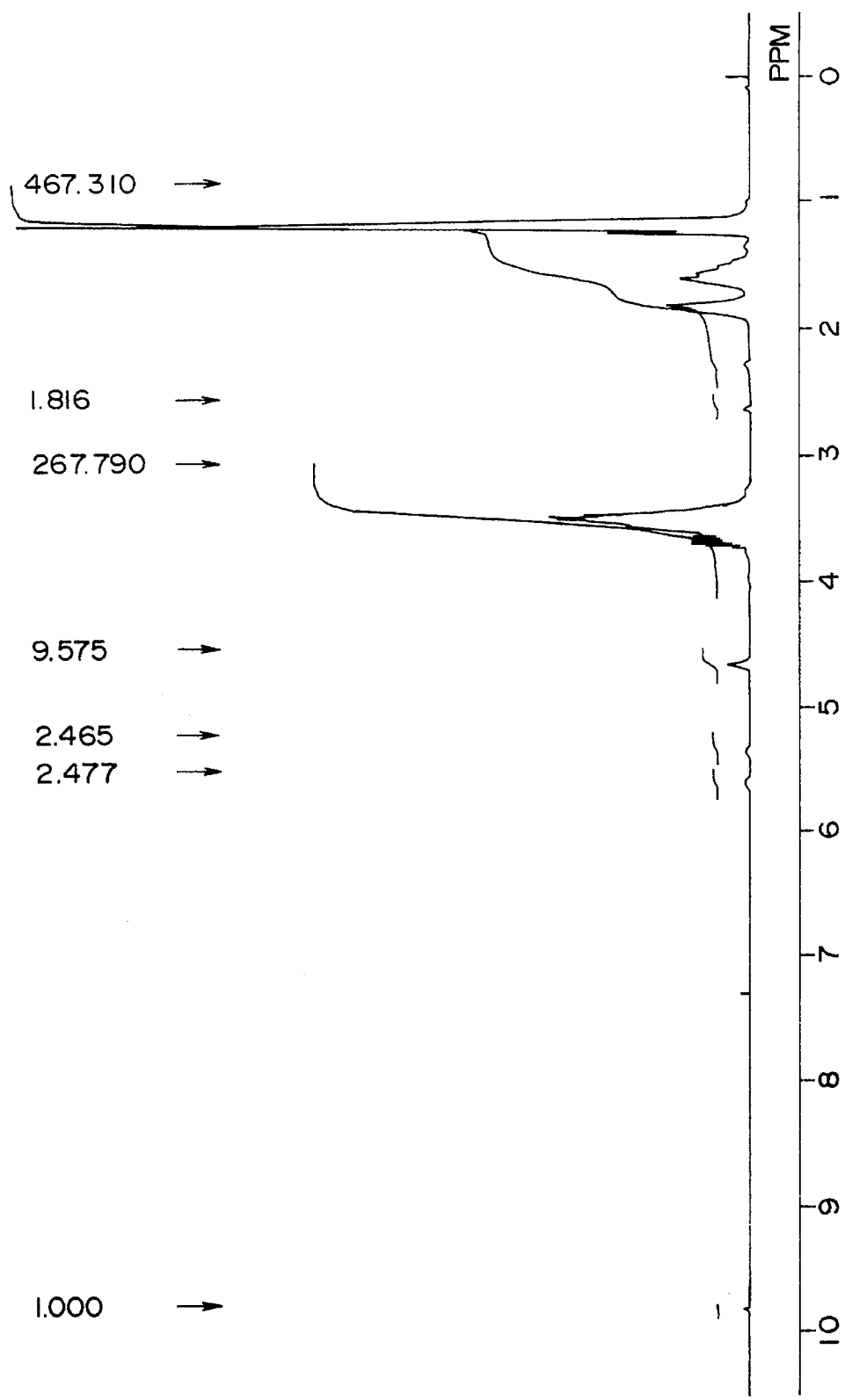

The infrared absorption spectrum is shown in FIG. 4, the $^{13}$C-NMR chart is shown in FIG. 5 and the $^1$H-NMR chart is shown in FIG. 6.

According to the same measurement as in Example 10, the end structure of the compound was a mixture of the formula (V) and the formula (VI) and the ratio of the numbers of molecule was: (V):(VI)=3.9:1.

EXAMPLE 12

Into a 5 liter glass flask equipped with a dropping funnel, a cooler and a stirrer, 1000 g of toluene, 450 g of acetaldehyde diethyl acetal and 4.5 g of boron trifluoride diethyl etherate were charged. Into a dropping funnel, 3200 g of ethyl vinyl ether was charged and dropped in 4 hours and 10 minutes. During this period, increase of the temperature of the reaction solution by the heat of reaction was observed and the temperature was kept at about 25° C. by cooling with an ice water bath. After finishing the dropping, the solution was further stirred for 5 minutes. The reaction mixture was transferred to a washing vessel and washed with 1000 ml of a 5 weight % aqueous solution of sodium hydroxide 3 times and then with 1000 ml of water 3 times. The solvent and unreacted materials were removed under the reduced pressure by using a rotary evaporator to obtain 3466 g of the polymer of ethyl vinyl ether. The product had color of light yellow.

Kinematic viscosity, average molecular weights, dispersion of molecular weight, compatibility with Flon and volume specific resistance of the polymer of ethyl vinyl ether obtained in the above were measured. The results are shown in Table 1.

Figure 7:
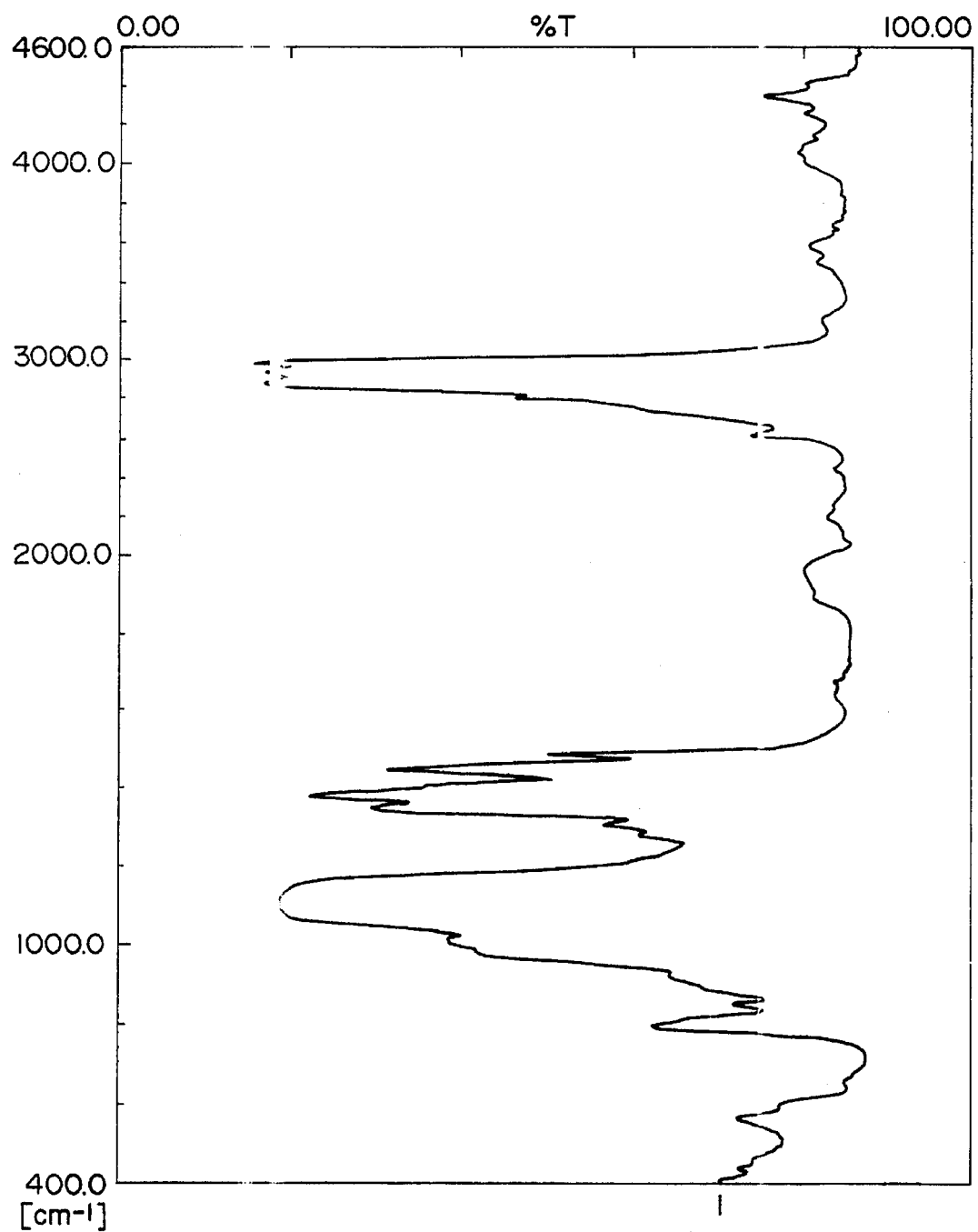

The infrared absorption spectrum is shown in FIG. 7.

EXAMPLE 13

Into a 5 liter glass flask equipped with a dropping funnel, a cooler and a stirrer, 1000 g of toluene, 195 g of ethanol and 4.5 g of boron trifluoride diethyl etherate were charged. Into a dropping funnel, 3875 g of ethyl vinyl ether was charged and dropped in 4 hours and 40 minutes. During this period, increase of the temperature of the reaction solution by the heat of reaction was observed and the temperature was kept at about 25° C. by cooling with an ice water bath. Until the amount of the monomer reached the equivalent amount to ethanol, the monomer was dropped slowly because there was an induction period for the heat generation. After finishing the dropping, the solution was further stirred for 5 minutes. The reaction mixture was transferred to a washing vessel and washed with 1100 ml of a 5 weight % aqueous solution of sodium hydroxide 3 times and then with 1100 ml of water 3 times. The solvent and unreacted materials were removed under the reduced pressure by using a rotary evaporator to obtain 3867 g of the polymer of ethyl vinyl ether. The product had color of light yellow.

Kinematic viscosity, average molecular weights, dispersion of molecular weight, compatibility with Flon and volume specific resistance of the polymer of ethyl vinyl ether obtained in the above were measured. The results are shown in Table 1.

Figure 8:
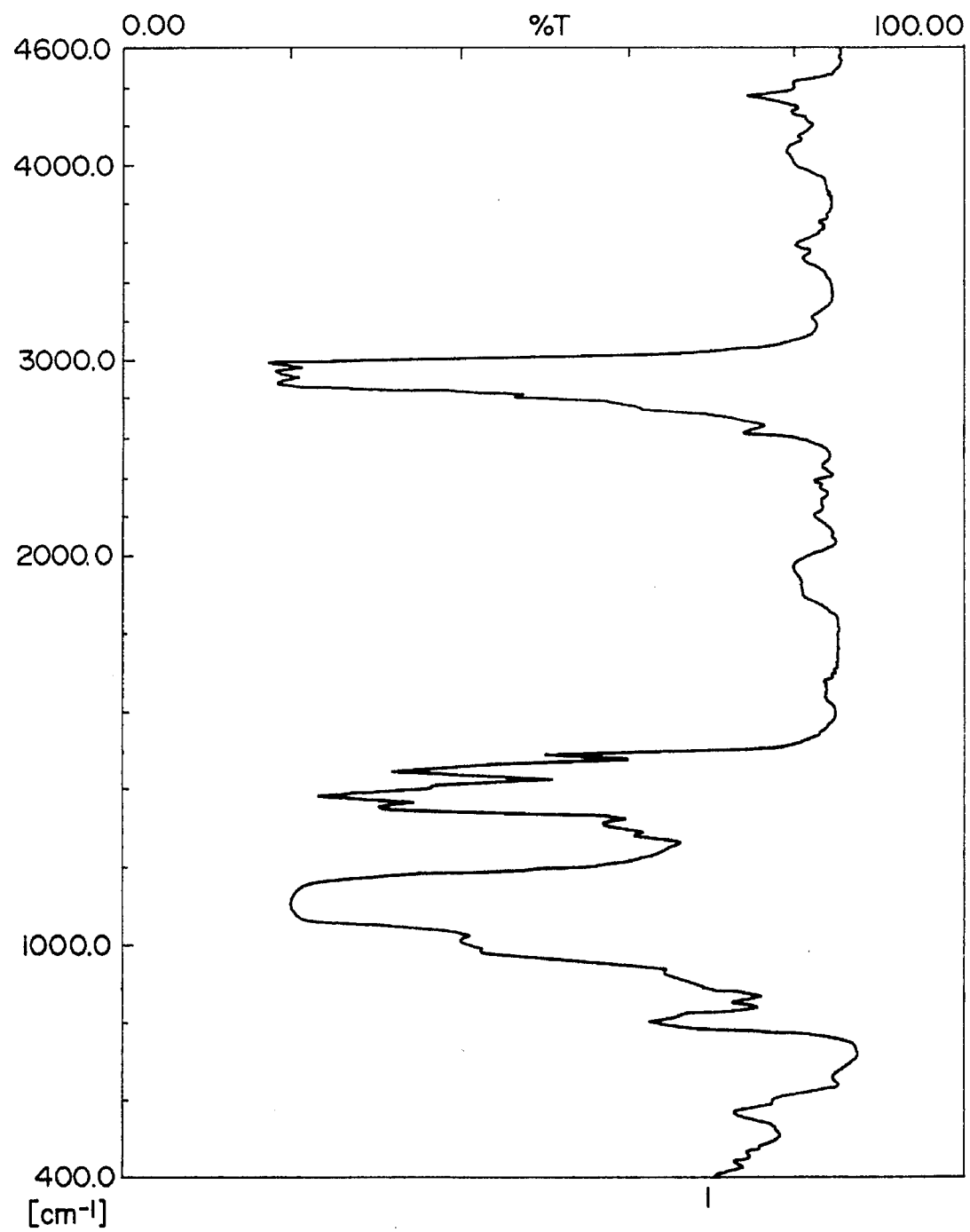
Figure 9:
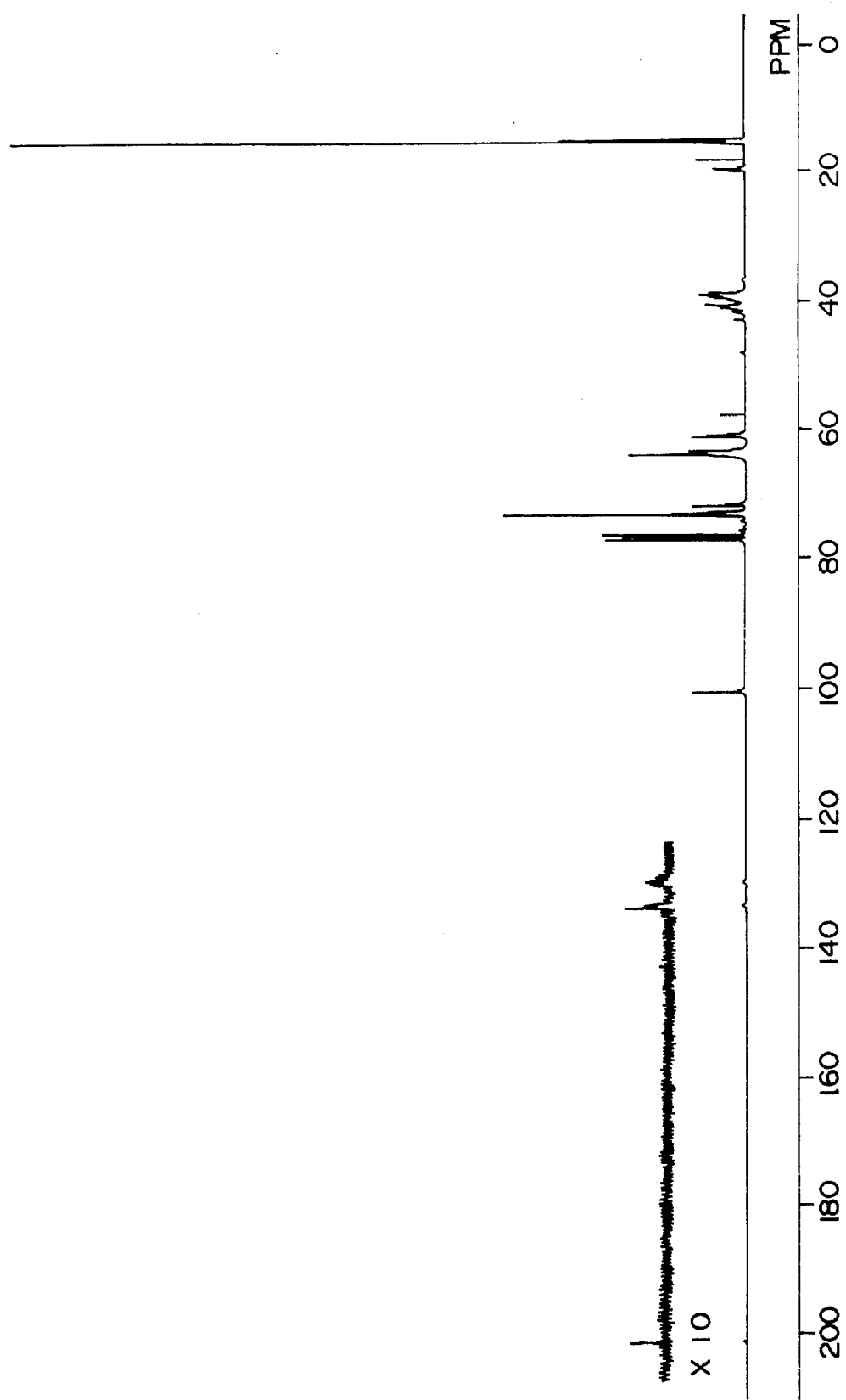
Figure 10:
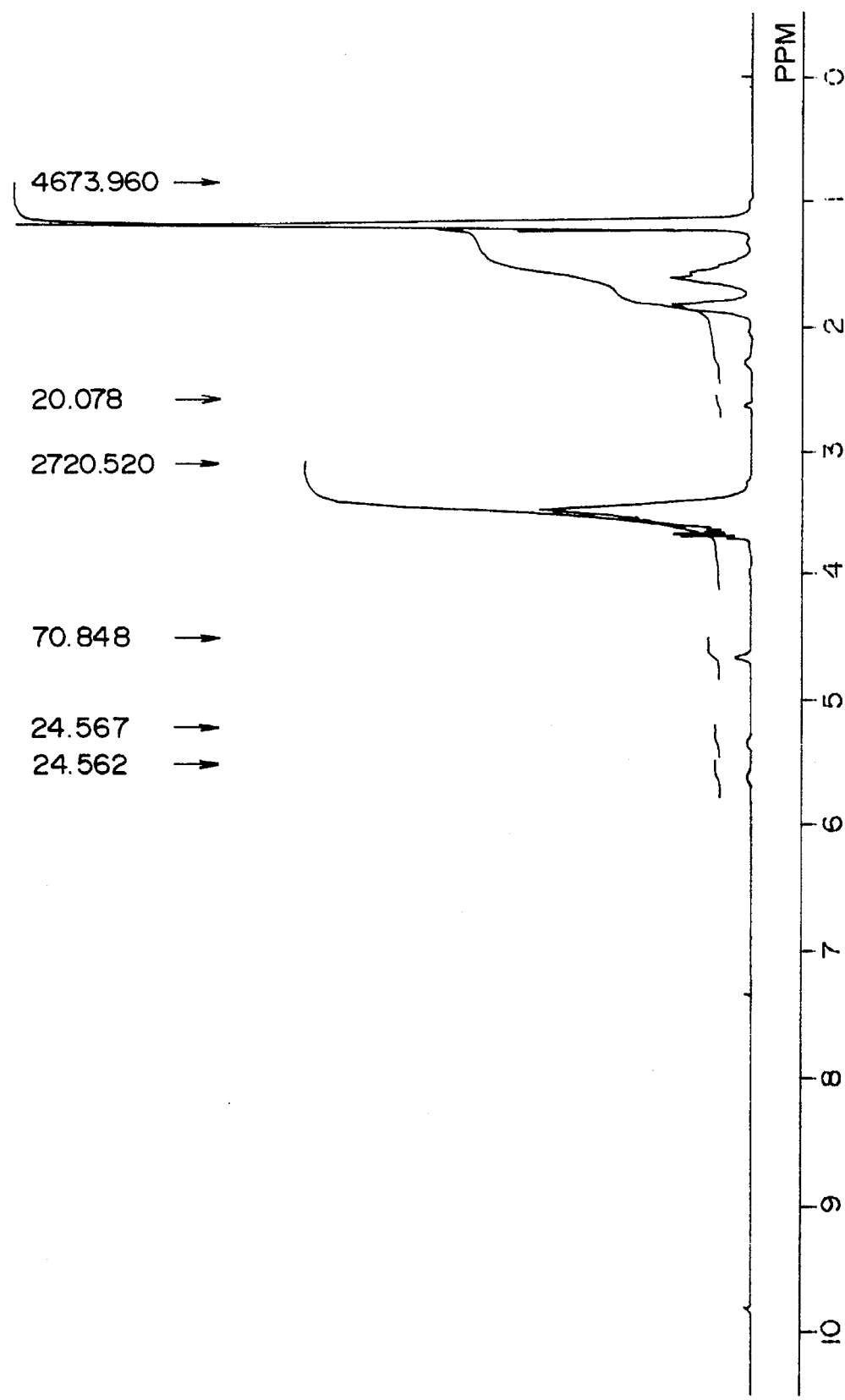

The infrared absorption spectrum is shown in FIG. 8, the 13C-NMR chart is shown in FIG. 9 and the $^1$H-NMR chart is shown in FIG. 10.

According to the same measurement as in Example 10, the end structure of the compound was a mixture of the formula (V) and the formula (VI) and the ratio of the numbers of molecule was: (V):(VI)=2.9:1.

EXAMPLE 14

Into a 500 ml glass flask equipped with a dropping funnel, a cooler and a stirrer, 125 g of toluene, 19.4 g of isopropyl alcohol and 2.3 g of boron trifluoride diethyl etherate were charged. Into a dropping funnel, 250 g of isopropyl vinyl ether was charged and dropped in 30 minutes. During this period, increase of the temperature of the reaction solution by the heat of reaction was observed and the temperature was kept at about 25° C. by cooling with an ice water bath. After finishing the dropping, the solution was further stirred for 5 minutes. The reaction mixture was transferred to a washing vessel and washed with 80 ml of a 5 weight % aqueous solution of sodium hydroxide 3 times and then with 80 ml of water 3 times. The solvent and unreacted materials were removed under the reduced pressure by using a rotary evaporator to obtain 238 g of the polymer of isopropyl vinyl ether. The product had color of light yellow.

Kinematic viscosity, average molecular weights, dispersion of molecular weight, compatibility with Flon and volume specific resistance of the polymer of isopropyl vinyl ether obtained in the above were measured. The results are shown in Table 1.

Figure 11:
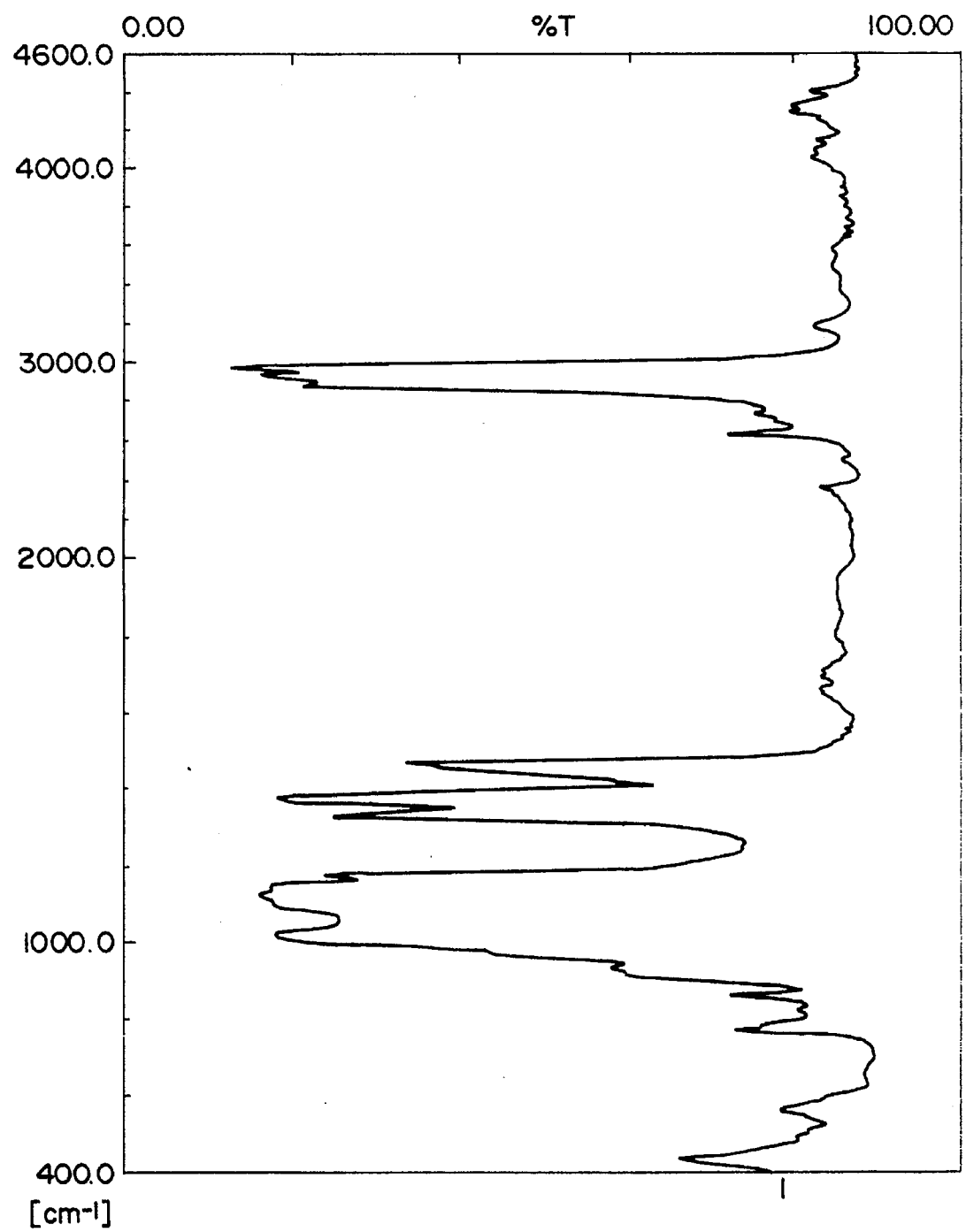

The infrared absorption spectrum is shown in FIG. 11.

EXAMPLE 15

Into a 500 ml glass flask equipped with a dropping funnel, a cooler and a stirrer, 125 g of toluene, 17.4 g of isopropyl alcohol and 2.1 g of boron trifluoride diethyl etherate were charged. Into a dropping funnel, 250 g of isopropyl vinyl ether was charged and dropped in 30 minutes. During this period, increase of the temperature of the reaction solution by the heat of reaction was observed and the temperature was kept at about 25° C. by cooling with an ice water bath. After finishing the dropping, the solution was further stirred for 5 minutes. The reaction mixture was transferred to a washing vessel and washed with 80 ml of a 5 weight % aqueous solution of sodium hydroxide 3 times and then with 80 ml of water 3 times. The solvent and unreacted materials were removed under the reduced pressure by using a rotary evaporator to obtain 236 g of the polymer of isopropyl vinyl ether. The product had color of light yellow.

Kinematic viscosity, average molecular weights, dispersion of molecular weight, compatibility with Flon and volume specific resistance of the polymer of isopropyl vinyl ether obtained in the above were measured. The results are shown in Table 1.

Figure 12:
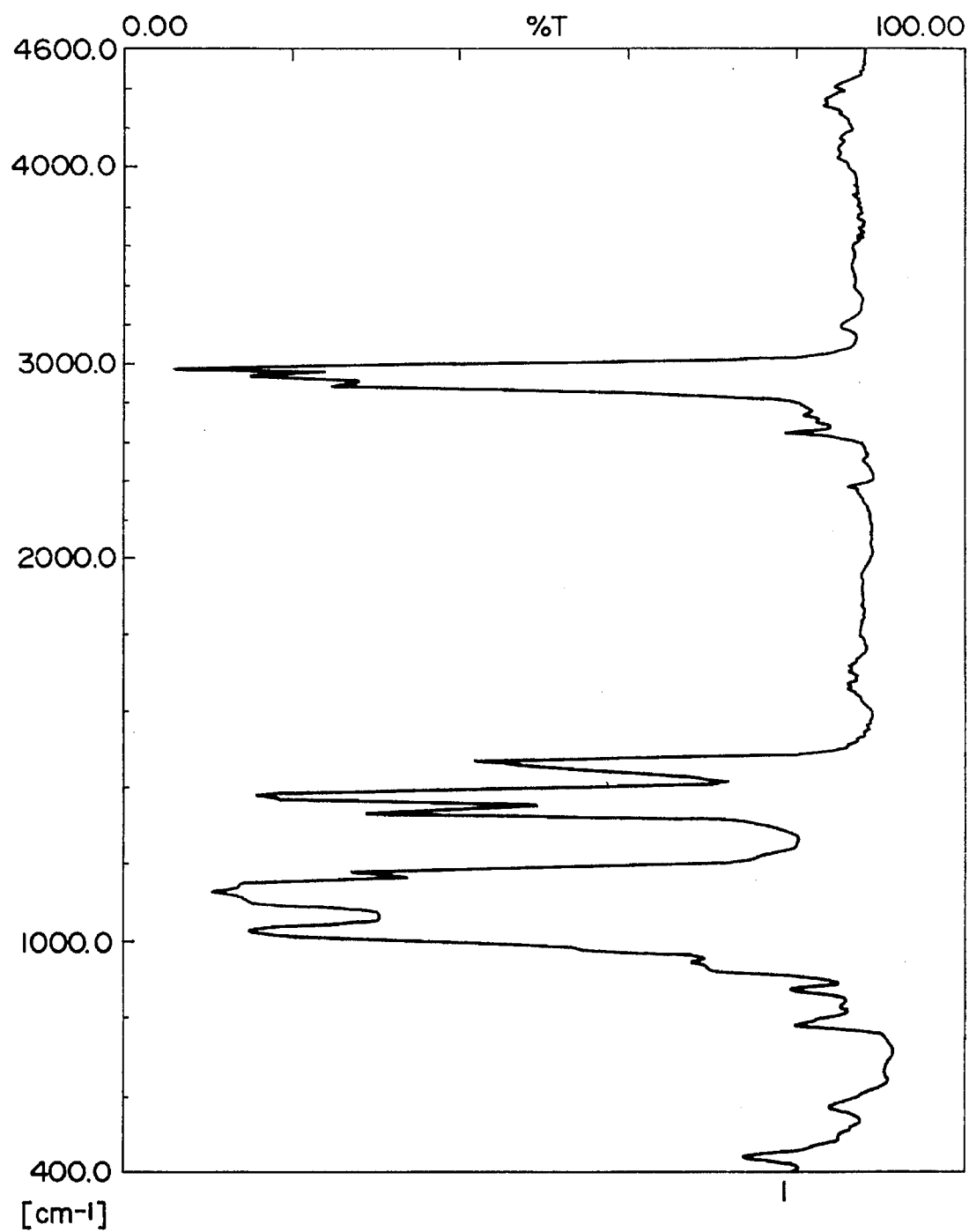
Figure 13:
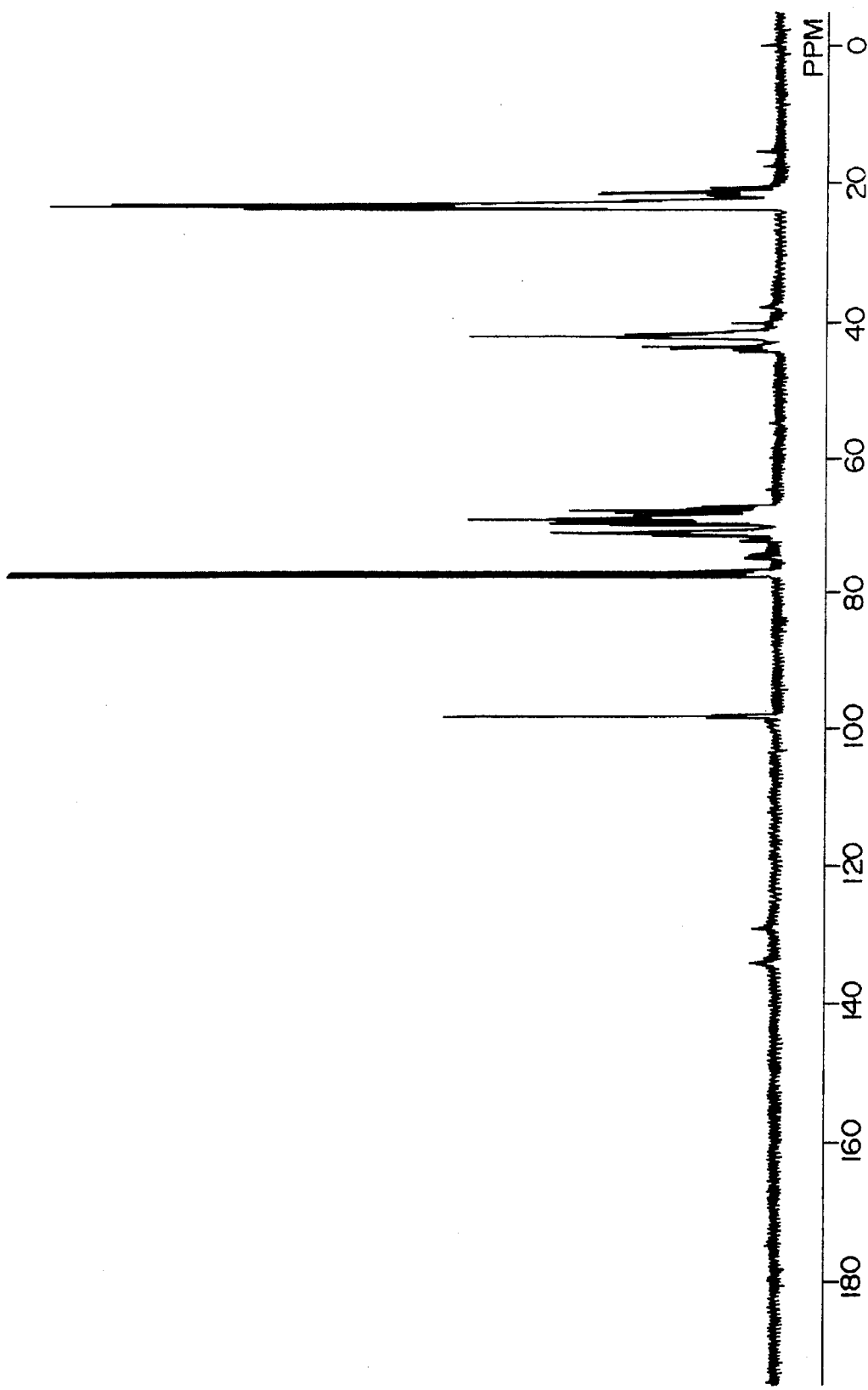
Figure 14:
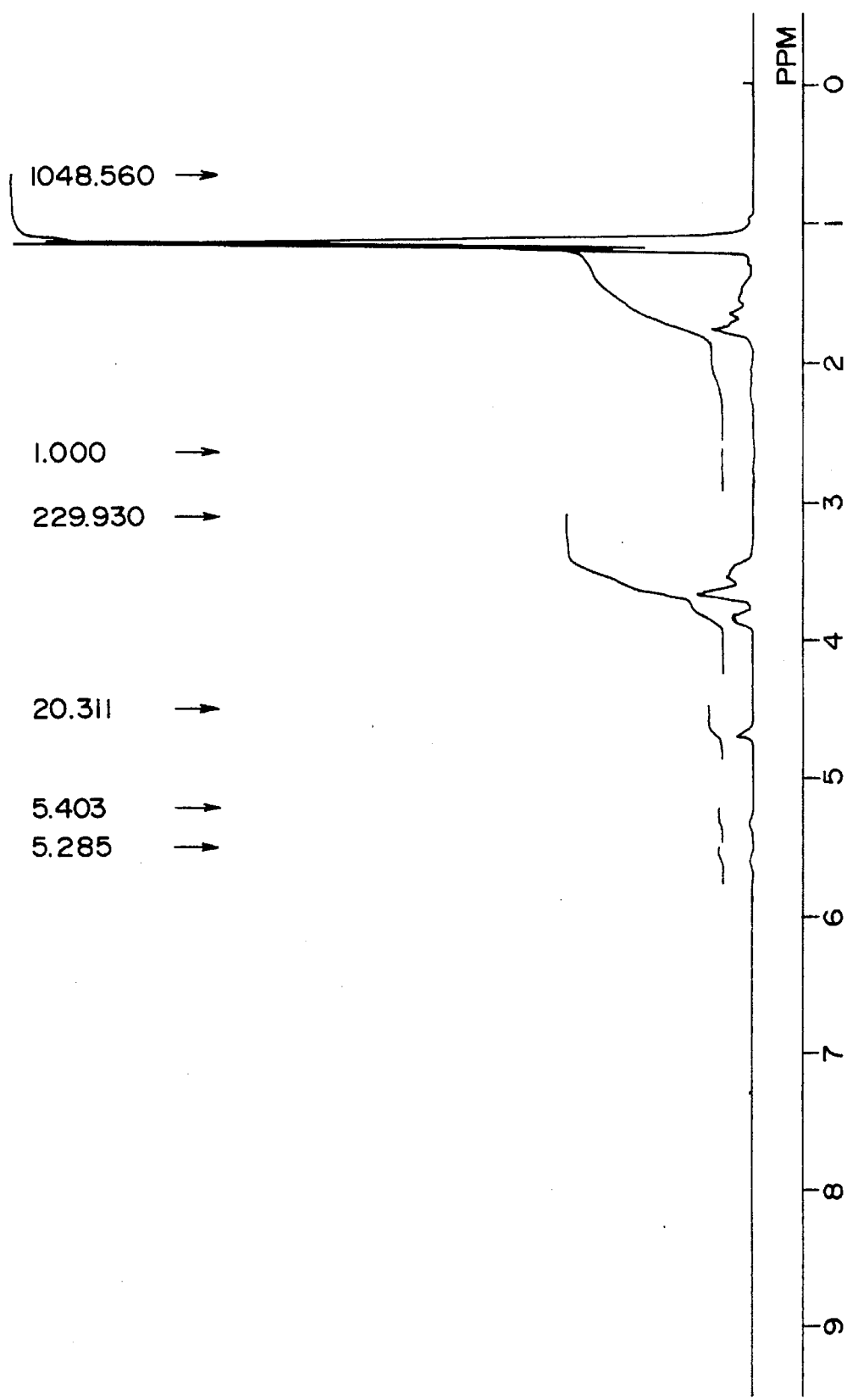

The infrared absorption spectrum is shown in FIG. 12, the $^{13}$C-NMR chart is shown in FIG. 13 and the $^1$H-NMR chart is shown in FIG. 14.

According to the same measurement as in Example 10, the end structure of the compound was a mixture of the formula (V) and the formula (VI) and the ratio of the numbers of molecule was: (V):(VI)=3.8:1.

EXAMPLE 16

Into a 200 ml stainless steel autoclave equipped with a stirrer, 40 g of toluene, 2.5 g of methanol and 0.18 g of boron trifluoride diethyl etherate were charged. After sealing the autoclave, the atmosphere in the autoclave was replaced with nitrogen. Into the autoclave, 47 g of methyl vinyl ether was added from a bomb by the pressure of the compound in 5 hours. During this period, increase of the temperature of the reaction solution by the heat of reaction was observed and the temperature was kept at about 25° C. by cooling with an ice water bath. After finishing the addition, the solution was further stirred for 5 minutes. The reaction mixture was transferred to a washing vessel and washed with 50 ml of a 5 weight % aqueous solution of sodium hydroxide 3 times and then with 100 ml of water 3 times. The solvent and unreacted materials were removed under the reduced pressure by using a rotary evaporator to obtain 42 g of the polymer of methyl vinyl ether. The product had color of light yellow.

Kinematic viscosity, average molecular weights, dispersion of molecular weight, compatibility with Flon and volume specific resistance of the polymer of methyl vinyl ether obtained in the above were measured. The results are shown in Table 1.

Figure 15:
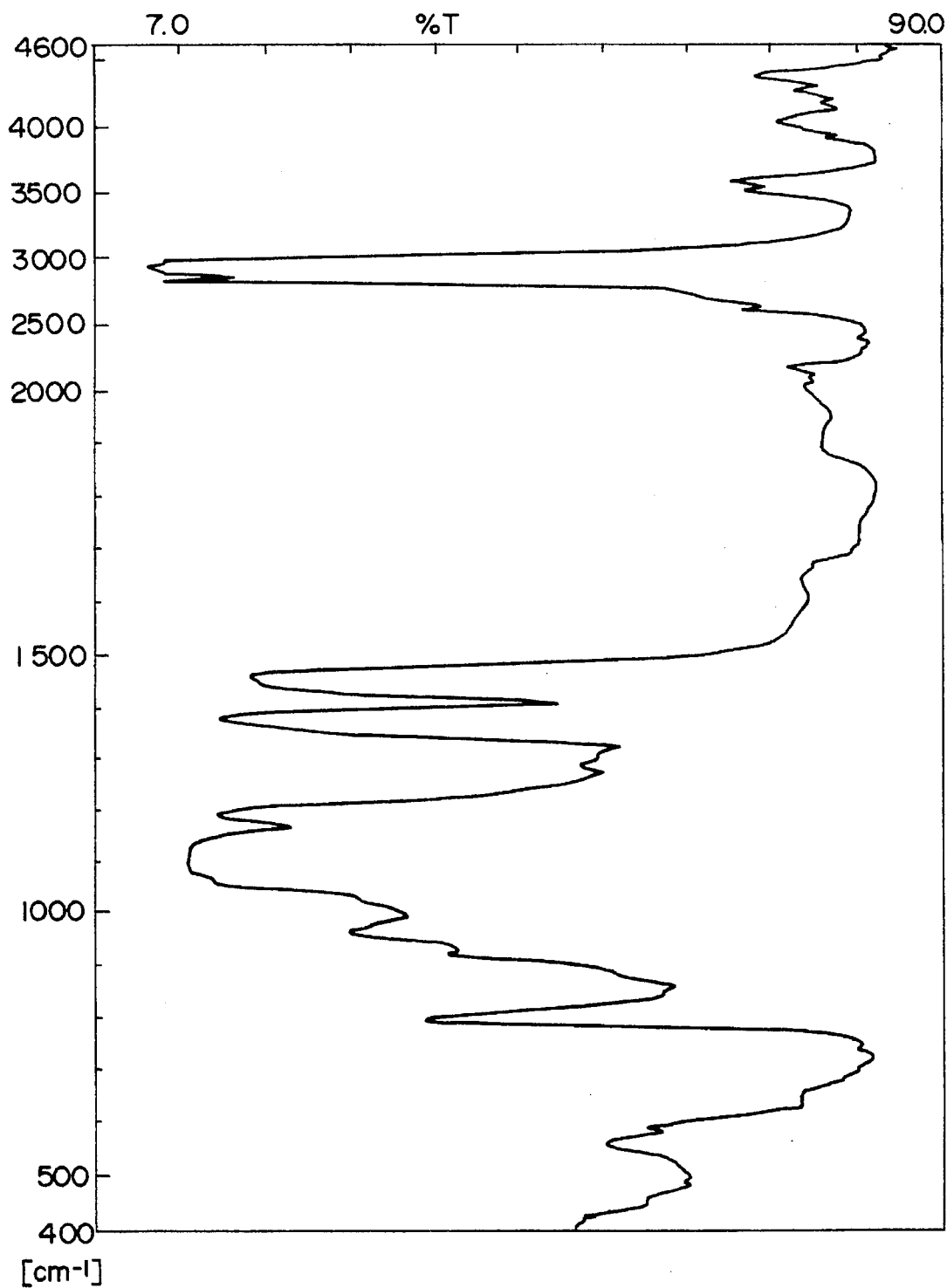
Figure 16:
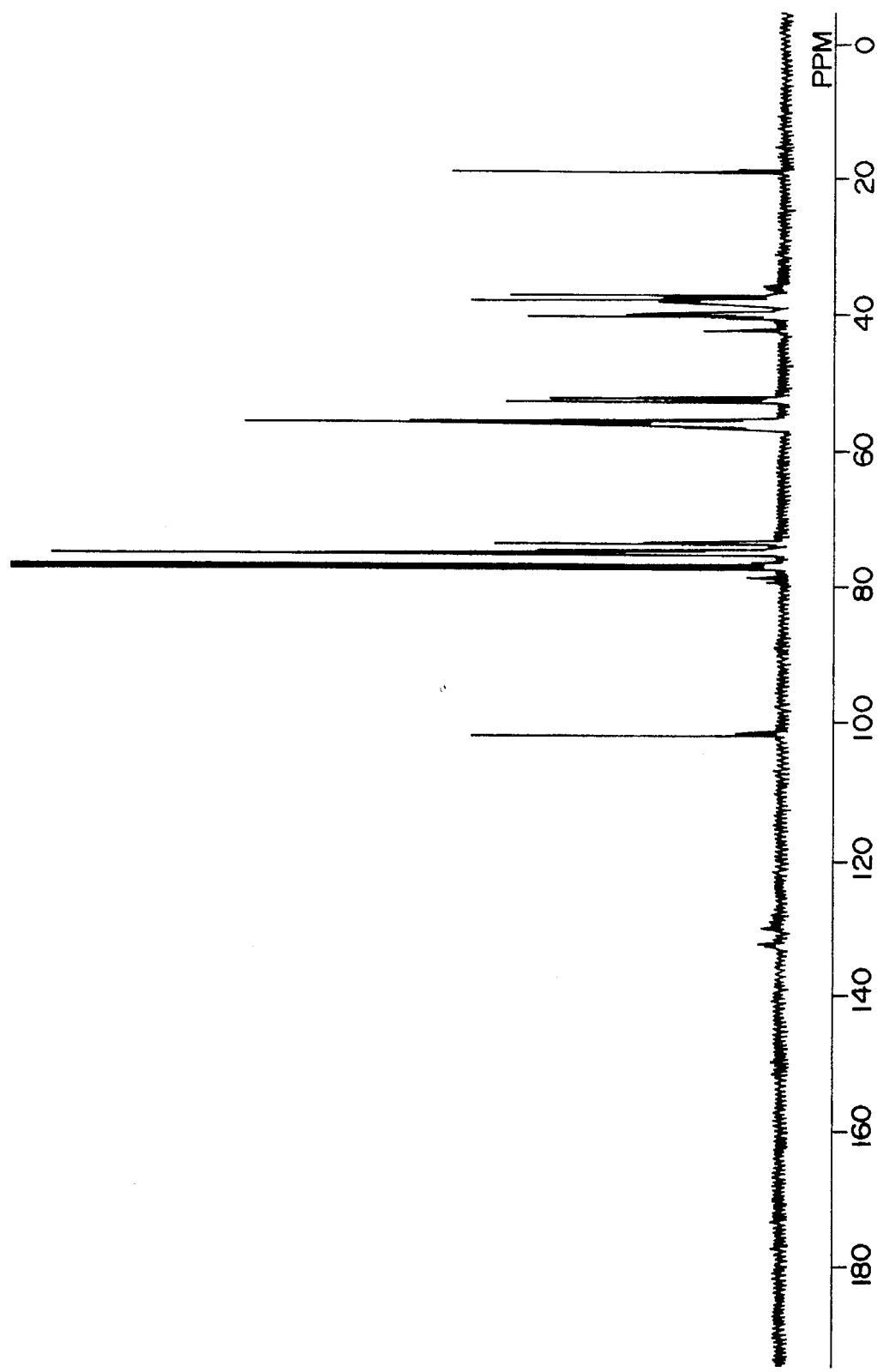
Figure 17:
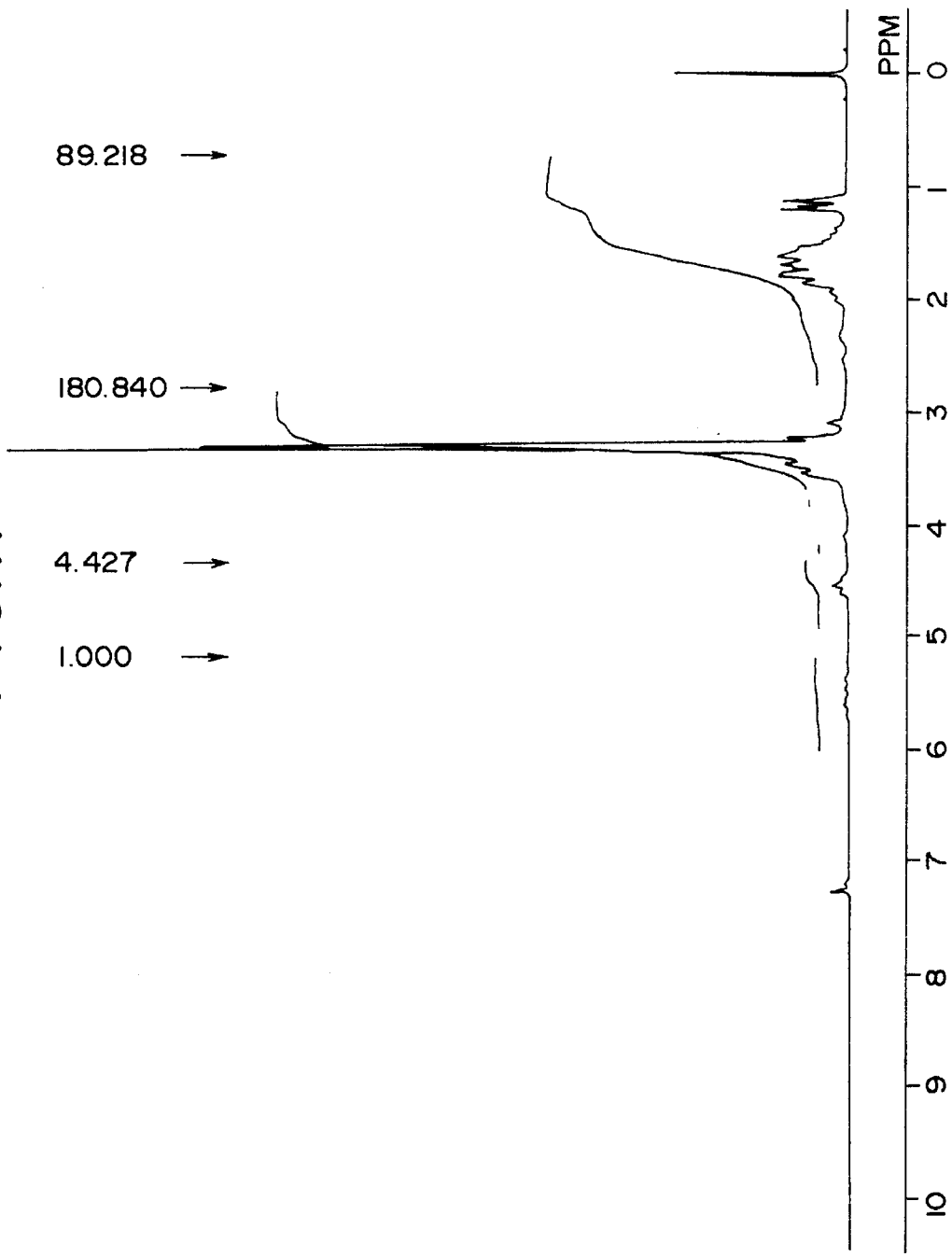

The infrared absorption spectrum is shown in FIG. 15, the $^{13}$C-NMR chart is shown in FIG. 16 and the $^1$H-NMR chart is shown in FIG. 17.

According to the same measurement as in Example 10, the end structure of the compound was a mixture of the formula (V) and the formula (VI) and the ratio of the numbers of molecule was: (V):(VI)=8.9:1.

EXAMPLE 17

Into a 500 ml glass flask equipped with a dropping funnel, a cooler and a stirrer, 50 g of toluene, 17.7 g of acetaldehyde diethyl acetal and 1.5 g of boron trifluoride diethyl etherate were charged. Into a dropping funnel, 43 g of ethyl vinyl ether and 65 g of isopropyl vinyl ether were charged and dropped in 50 minutes. The temperature of the reaction solution increased by the heat of reaction and the temperature was kept at about 25° C. by cooling with an ice water bath. After finishing the dropping, the solution was further stirred for 5 minutes. The reaction mixture was transferred to a washing vessel and washed with 100 ml of a 5 weight % aqueous solution of sodium hydroxide 3 times and then with 150 ml of water 3 times. The solvent and unreacted materials were removed under the reduced pressure by using a rotary evaporator to obtain 120 g of the crude product. The product had color of light yellow.

Kinematic viscosity, average molecular weights, dispersion of molecular weight, compatibility with Flon and volume specific resistance of the polymer of ethyl vinyl ether/isopropyl vinyl ether copolymer obtained in the above were measured. The results are shown in Table 1.

Figure 18:
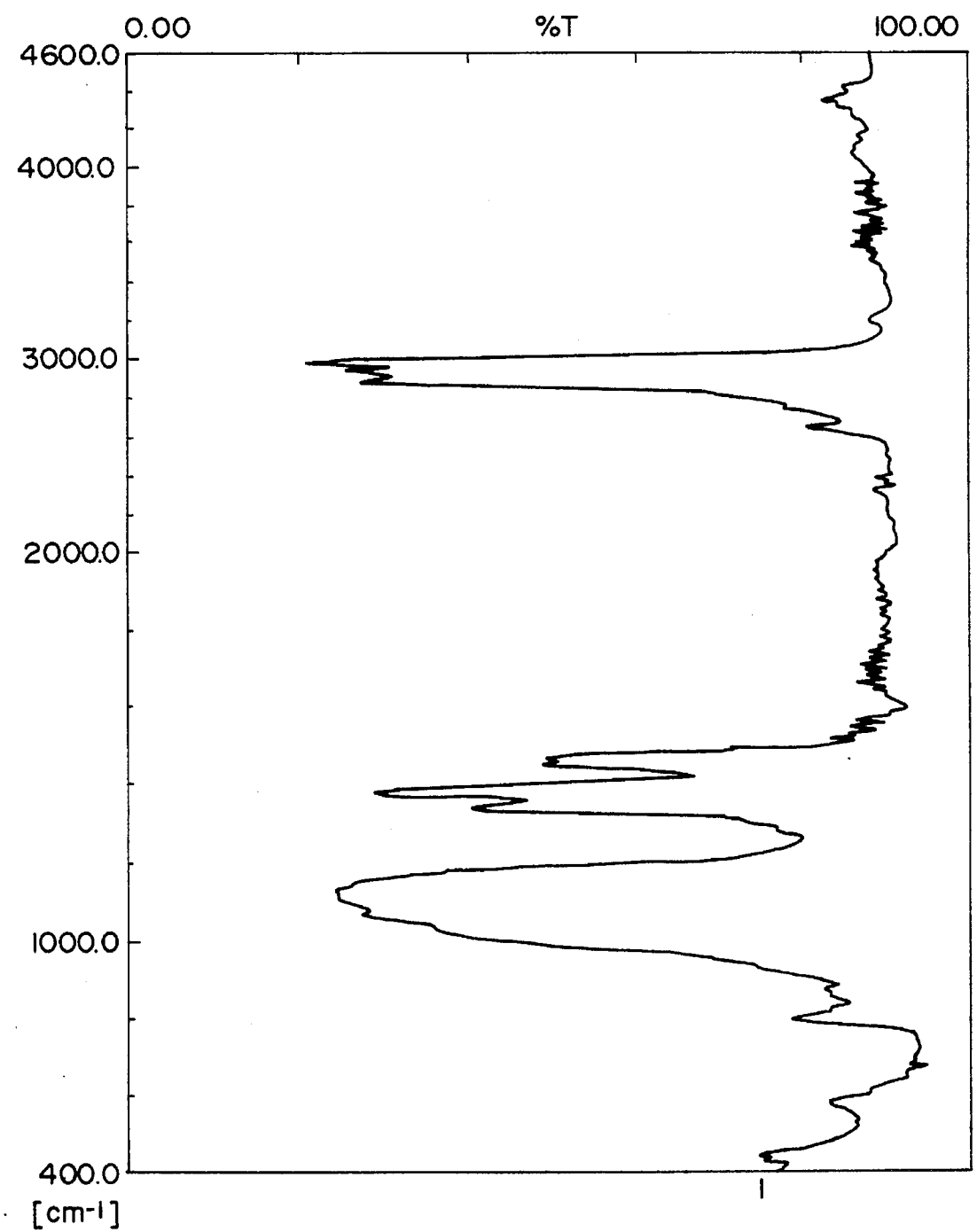
Figure 19:
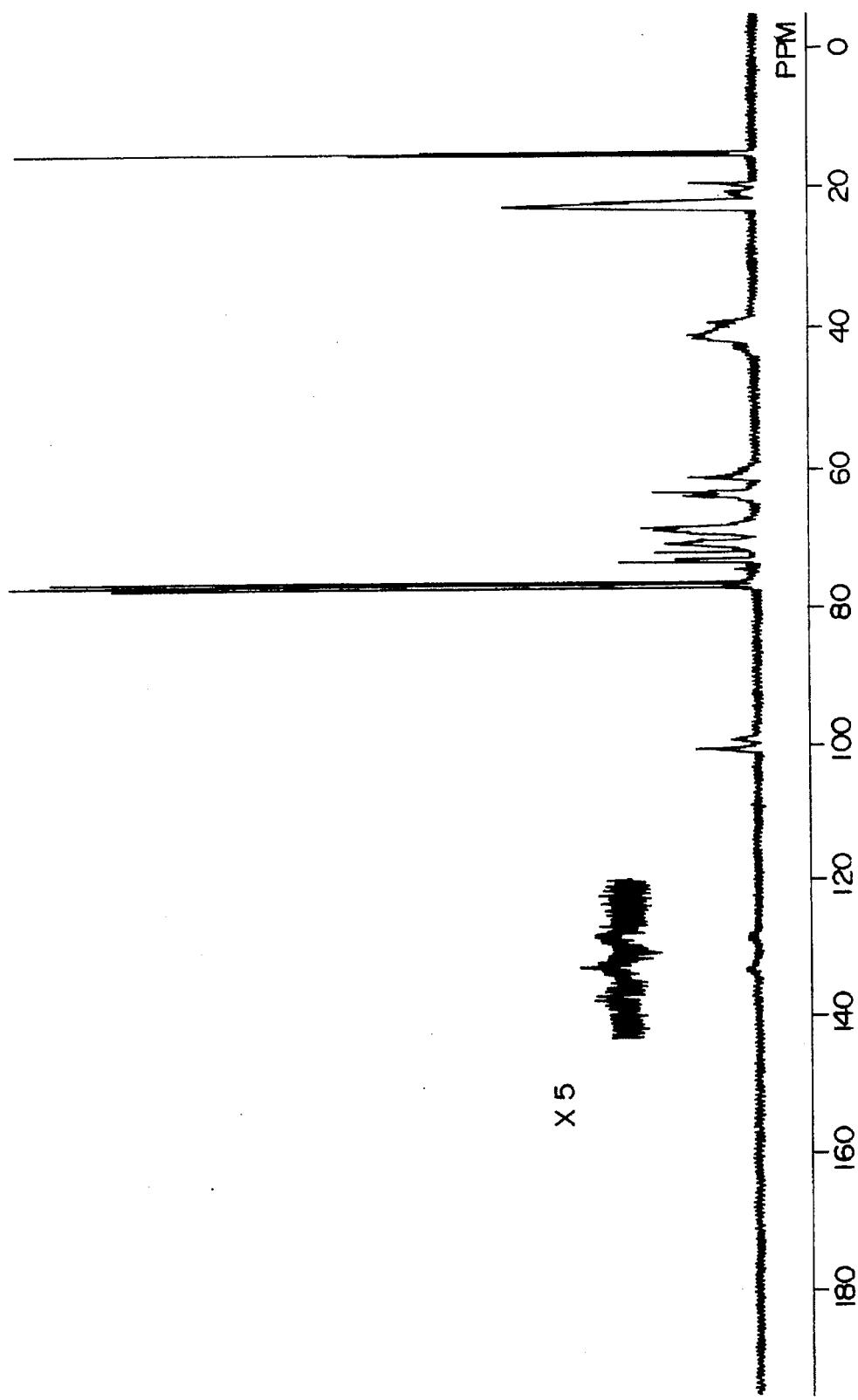
Figure 20:
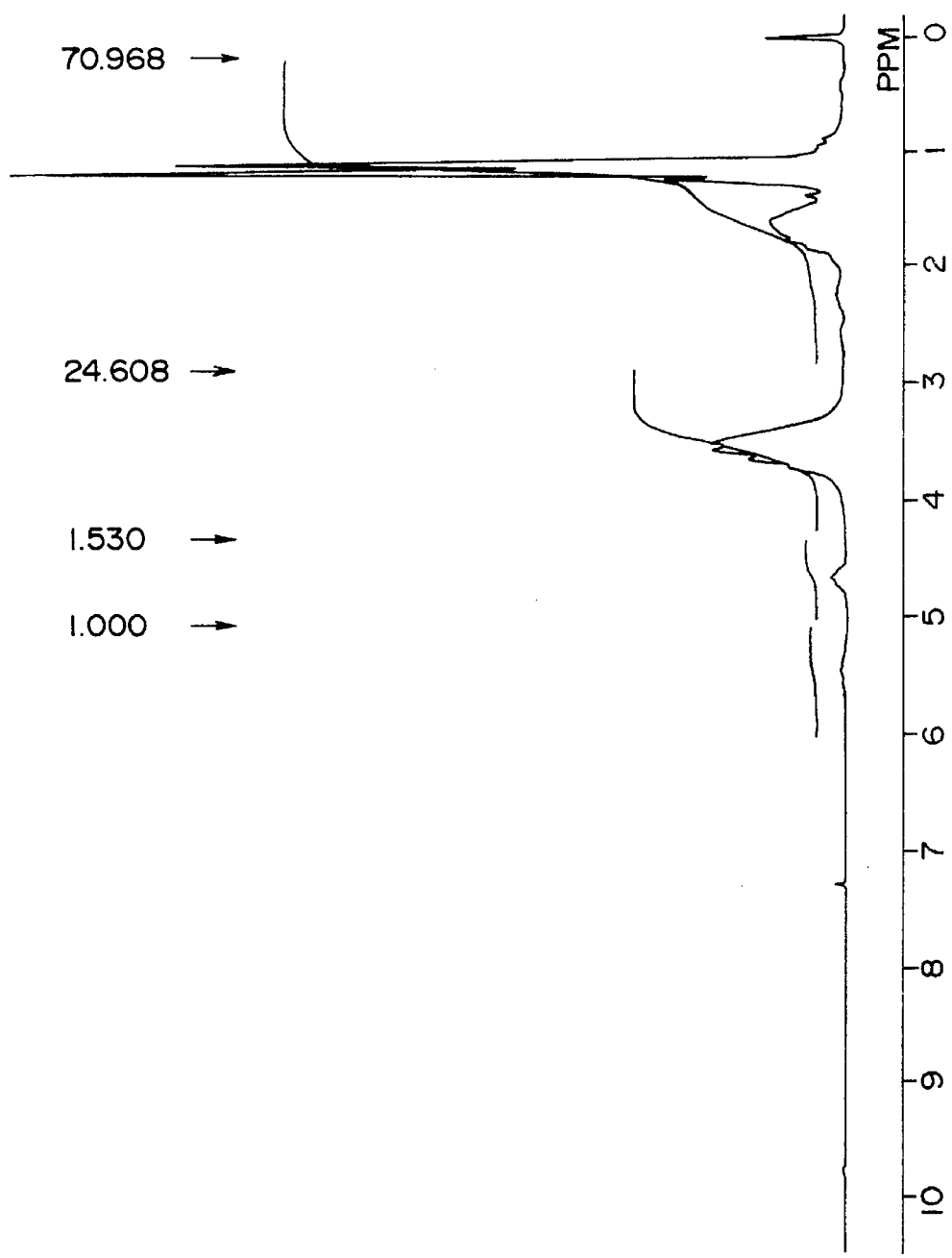

The infrared absorption spectrum is show in FIG. 18, the $^{13}$C-NMR chart is shown in FIG. 19 and the $^{1}$H-NMR chart is shown in FIG. 20.

According to the same measurement as in Example 10, the end structure of the compound was a mixture of the formula (V) and the formula (VI) and the ratio of the numbers of molecule was: (V):(VI)=3.1:1.

EXAMPLE 18

Into a 500 ml glass flask equipped with a dropping funnel, a cooler and a stirrer, 50 g of toluene, 4.6 g of ethyl alcohol and 0.2 g of boron trifluoride diethyl etherate were charged. Into a dropping funnel, 86 g of 1-ethoxy-1-propene was charged and dropped in 50 minutes. During this period, increase of the temperature of the reaction solution by the heat of reaction was observed and the temperature was kept at about 30° C. by cooling with an ice water bath. After finishing the dropping, the solution was further stirred for 30 minutes. The reaction mixture was transferred to a washing vessel and washed with 100 ml of a 5 weight % aqueous solution of sodium hydroxide 3 times and then with 150 ml of water 3 times. The solvent and unreacted materials were removed under the reduced pressure by using a rotary evaporator to obtain 84 g of the polymer of 1-ethoxy-1-propene.

Kinematic viscosity, average molecular weights, dispersion of molecular weight, compatibility with Flon and volume specific resistance of the polymer of 1-ethoxy-1-propene obtained in the above were measured. The results are shown in Table 1.

Figure 21:
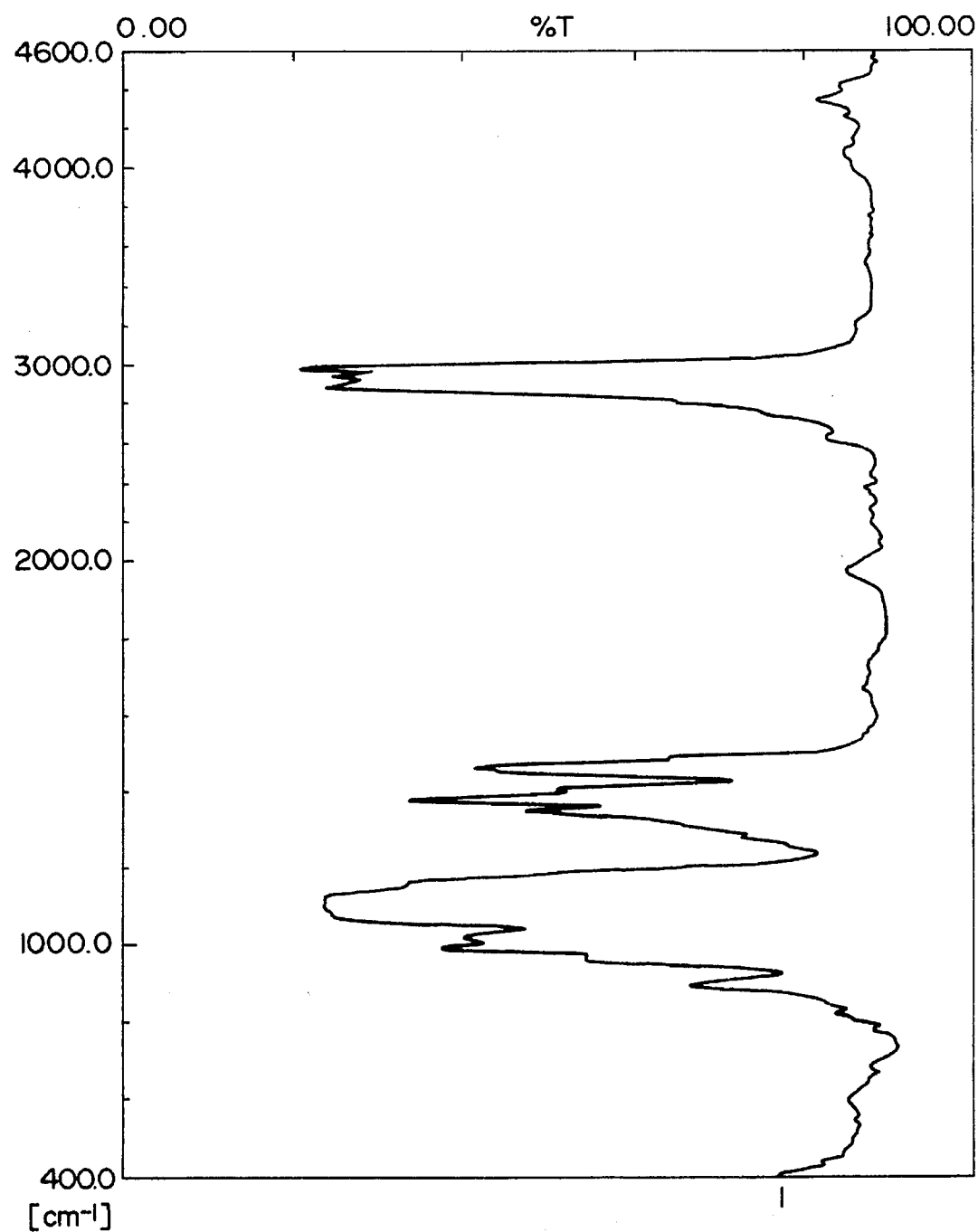
Figure 22:
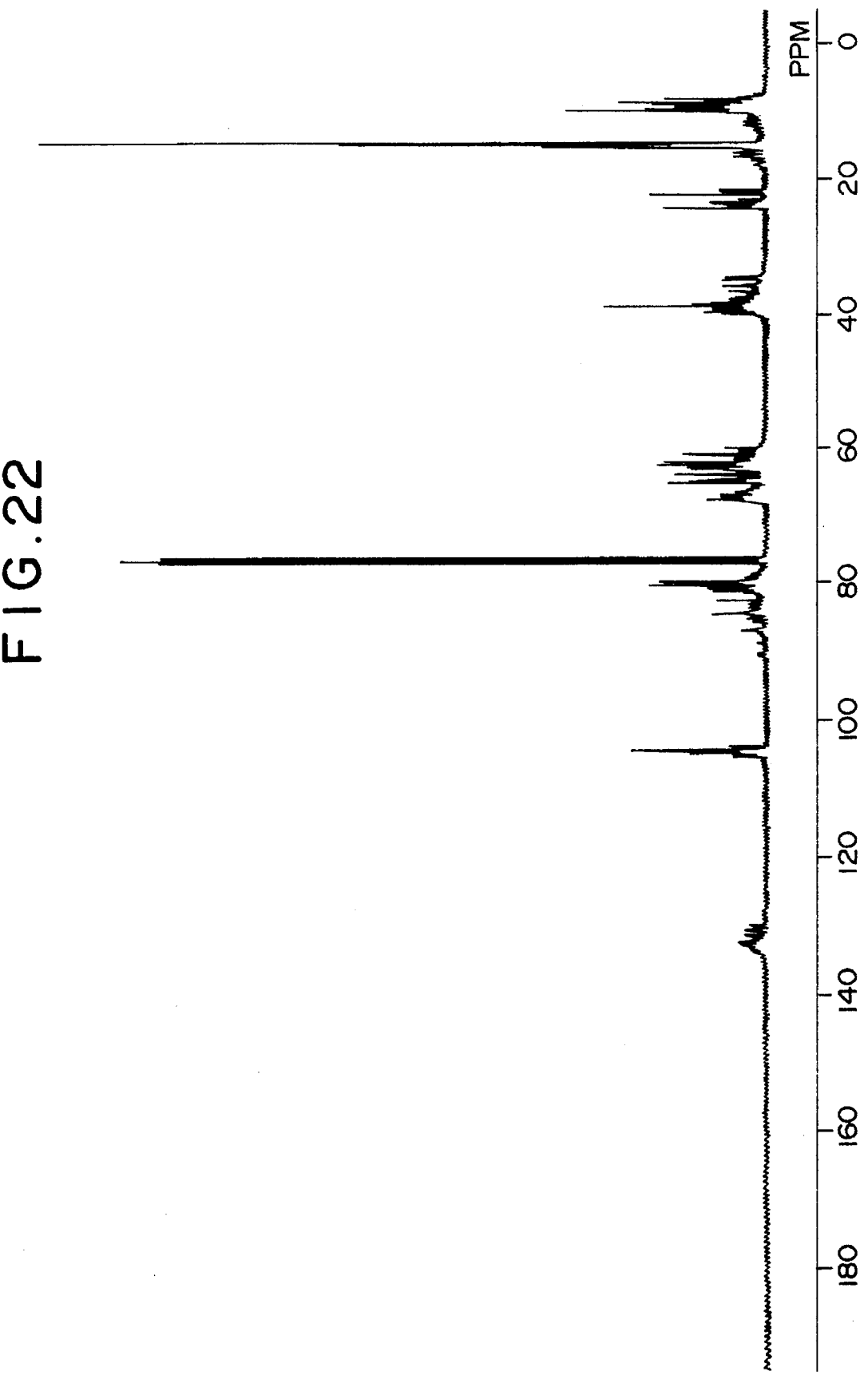
Figure 23:
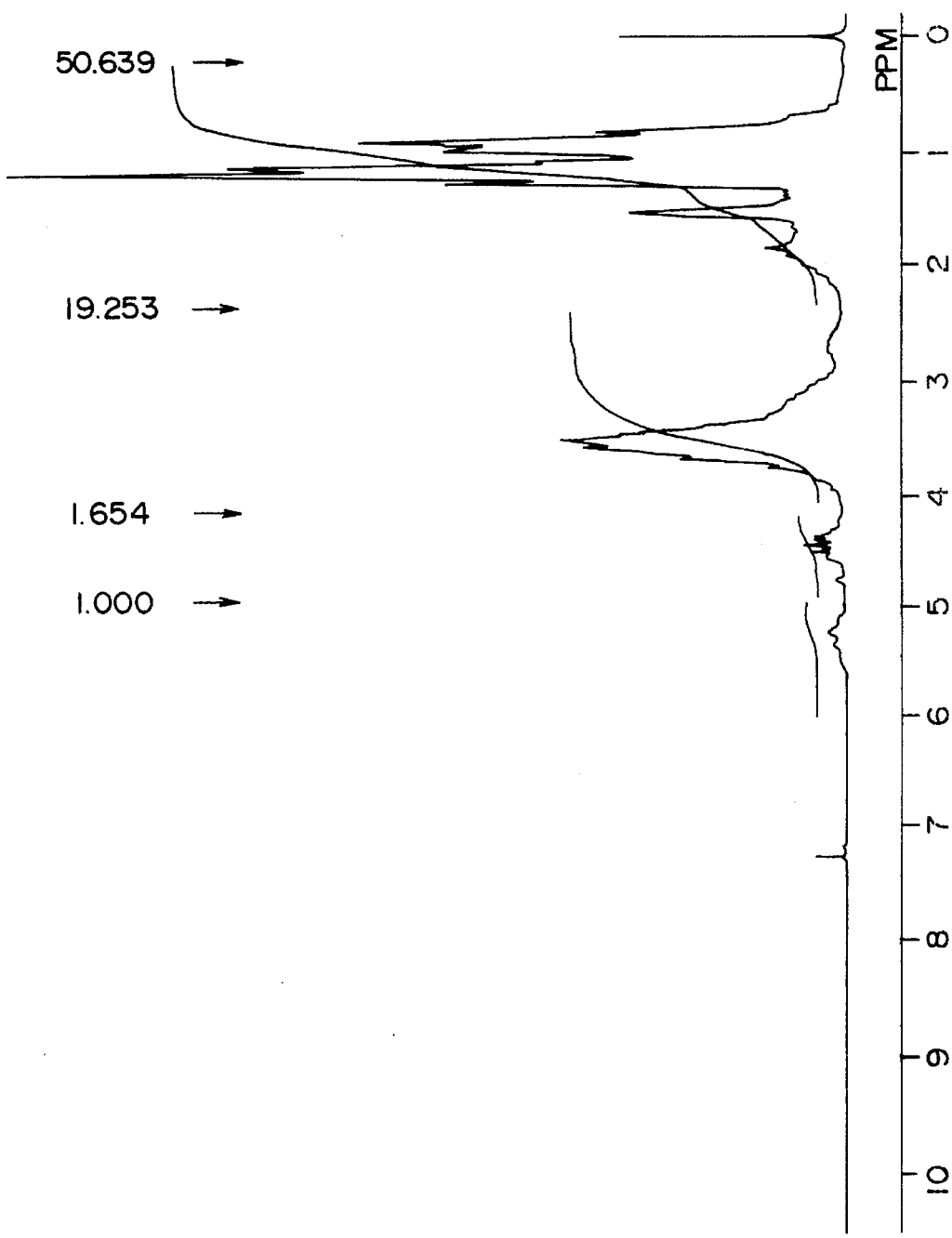

The infrared absorption spectrum is shown in FIG. 21, the $^{13}$C-NMR chart is shown in FIG. 22 and the $^{1}$H-NMR chart is shown in FIG. 23.

TABLE 1

| | kinematic viscosity (cSt) | | molecular weight | | |
|---|---|---|---|---|---|
| | 40° C. | 100° C. | weight average | number average | dispersion |
| Example 10 | 19.5 | 3.56 | 481 | 443 | 1.08 |
| Example 11 | 44.3 | 5.83 | 639 | 548 | 1.17 |
| Example 12 | 76.1 | 8.29 | 769 | 640 | 1.20 |
| Example 13 | 109.5 | 10.30 | 848 | 703 | 1.21 |
| Example 14 | 28.9 | 4.41 | 576 | 490 | 1.18 |
| Example 15 | 36.9 | 4.85 | 609 | 513 | 1.19 |
| Example 16 | 91.9 | 8.53 | 581 | 418 | 1.39 |
| Example 17 | 48.8 | 6.05 | 722 | 547 | 1.33 |
| Example 18 | 25.6 | 3.88 | 425 | 384 | 1.11 |

TABLE 1-continued

| | compatibility with Flon 134a | | | | volume specific resistance at 80° C. |
|---|---|---|---|---|---|
| | temperature of separation at low temperature (°C.) | | temperature of separation at high temperature (°C.) | | |
| | 5% | 10% | 5% | 10% | (Ω · cm) |
| Example 10 | −60.0> | −60.0> | 80.0< | 80.0< | $2.0 \times 10^{12}$ |
| Example 11 | −60.0> | −60.0> | 80.0< | 80.0< | $3.2 \times 10^{12}$ |
| Example 12 | −60.0> | −60.0> | 80.0< | 80.0< | $2.7 \times 10^{12}$ |
| Example 13 | −60.0> | −60.0> | 80.0< | 80.0< | $2.2 \times 10^{12}$ |
| Example 14 | −60.0> | −60.0> | 80.0< | 80.0< | $4.5 \times 10^{12}$ |
| Example 15 | −60.0> | −60.0> | 80.0< | 80.0< | $3.8 \times 10^{12}$ |
| Example 16 | −60.0> | −60.0> | 80.0< | 80.0< | $2.5 \times 10^{12}$ |
| Example 17 | −60.0> | −60.0> | 80.0< | 80.0< | $1.4 \times 10^{12}$ |
| Example 18 | −40.0 | −40.0 | 80.0< | 80.0< | $1.2 \times 10^{11}$ |

What is claimed is:

1. A method of production of a polyvinyl ether compound for a lubricating oil comprising the steps of:

(a) charging a boron trifluoride or a complex thereof, a solvent and an alcohol expressed by the general formula (III):

$$R^{14}(OR^{13})_p OH \qquad (III)$$

wherein $R^{13}$ is a bivalent hydrocarbon group having 2 to 10 carbon atoms, $R^{14}$ is a hydrocarbon group having 1 to 10 carbon atoms, p is a number the average of which is in the range of 0 to 10 and a plural of $R^{13}O$'s may be the same or different from each other when a plural of $R^{13}O$'s are present, into a reactor to form a mixture therein;

(b) forming an acetal expressed by the general formula (II'):

$$\begin{array}{c} R^1 \quad R^3 \\ | \quad | \\ HC-C-O(R^{13}O)_p R^{14} \\ | \quad | \\ R^2 \quad O(R^4O)_k R^5 \end{array} \qquad (II')$$

wherein $R^1$, $R^2$ and $R^3$ are a hydrogen atom or a hydrocarbon group having 1 to 8 carbon atoms, respectively, and may be the same or different from each other, $R^4$ is a bivalent hydrocarbon group having 2 to 10 carbon atoms, $R^5$ is a hydrocarbon group having 1 to 10 carbon atoms, $R^{13}$ and $R^{14}$ are the same as described above, k is the number the average of which is in the range of 0 to 10, a plural of $R^4O$'s may be the same or different from each other when a plural of $R^4O$'s are present and a plural of $R^{13}O$'s may be the same or different from each other when a plural of $R^{13}O$'s are present, by adding gradually a vinyl ether monomer, until the amount of the monomer reaches the equivalent amount to said alcohol, expressed by the general formula (I):

$$\begin{array}{c} R^1-C=C-R^3 \\ | \quad | \\ R^2 \quad O(R^4O)_k R^5 \end{array} \qquad (I)$$

wherein $R^1$ to $R^5$ and k are the same as those described above and a plural of $R^4O$'s may be the same or different from each other when a plural of $R^4O$'s are present, to the mixture formed in step (a) at a temperature of 0° to 100° C.; and (c) forming a polyvinyl ether compound having a weight average molecular weight in the range of 300 to 1200 and ratio of weight average molecular weight and number average molecular weight in the range of 1.05 to 1.50 by further adding vinyl ether monomer expressed by said general formula (I) to the resulting mixture provided in the reactor in step (b), with a speed which balances with the ability of the reactor to eliminate the heat of polymerization, at a temperature of 0° to 100° C.

* * * * *